US012778575B2

(12) United States Patent
Jacobs et al.

(10) Patent No.: US 12,778,575 B2
(45) Date of Patent: Nov. 3, 2026

(54) KNOTLESS ANCHOR INSERTER TOOL EXTRACTION

(71) Applicant: Medos International Sarl, Le Locle (CH)

(72) Inventors: Jordan Jacobs, Raynham, MA (US); Ravi Patel, Providence, RI (US); Mark Shainwald, Raynham, MA (US); Timothy Reppert, Foster City, CA (US)

(73) Assignee: Medos International Sarl, Le Locle (CH)

( * ) Notice: Subject to any disclaimer, the term of this patent is extended or adjusted under 35 U.S.C. 154(b) by 127 days.

(21) Appl. No.: 18/909,359

(22) Filed: Oct. 8, 2024

(65) Prior Publication Data

US 2025/0032112 A1 Jan. 30, 2025

Related U.S. Application Data

(63) Continuation of application No. 17/565,514, filed on Dec. 30, 2021, now Pat. No. 12,137,894.

(51) Int. Cl.
*A61B 17/04* (2006.01)
*A61B 17/00* (2006.01)

(52) U.S. Cl.
CPC ..................... *A61B 17/0401* (2013.01); *A61B 2017/00367* (2013.01); *A61B 2017/0409* (2013.01); *A61B 2017/0445* (2013.01)

(58) Field of Classification Search
CPC ........ A61B 17/0401; A61B 2017/0409; A61B 2017/0445; A61B 2017/044; A61B 2017/0408; A61B 2017/0412; A61B 17/00
See application file for complete search history.

(56) References Cited

U.S. PATENT DOCUMENTS

| | | | |
|---|---|---|---|
| 5,092,870 A | 3/1992 | Mittermeier | |
| 5,171,314 A | 12/1992 | Dulebohn | |
| 5,366,133 A | 11/1994 | Geiste | |
| 5,499,991 A | 3/1996 | Garman et al. | |
| 5,569,269 A | 10/1996 | Hart et al. | |
| 5,645,566 A | 7/1997 | Brenneman et al. | |
| D387,161 S | 12/1997 | Ferragamo et al. | |

(Continued)

FOREIGN PATENT DOCUMENTS

| | | |
|---|---|---|
| EP | 2422712 A2 | 2/2012 |
| EP | 3069663 A1 | 9/2016 |

(Continued)

OTHER PUBLICATIONS

Harvey Tool, "Thread Milling Cutters—Multi-Form—N.P.T. Threads," dated no later than Apr. 10, 2021, available at <https://www.harveytool.com/products/thread-milling-cutters---multi-form---n.p.t.-threads> (2 pages).

(Continued)

*Primary Examiner* — Katherine M Shi
(74) *Attorney, Agent, or Firm* — Barnes & Thornburg LLP

(57) ABSTRACT

Various exemplary devices, systems, and methods for knotless anchor inserter tool extraction are provided. In general, an inserter tool is configured for knotless anchor insertion in a soft tissue repair surgical procedure. The inserter tool is configured to insert an anchor into a bone of a patient to secure a soft tissue relative to the bone. The inserter tool includes a retraction mechanism configured to cause the inserter tool to be removed from within the anchor.

10 Claims, 24 Drawing Sheets

(56) References Cited

U.S. PATENT DOCUMENTS

| | | | |
|---|---|---|---|
| 5,707,394 | A | 1/1998 | Miller et al. |
| 5,752,964 | A | 5/1998 | Mericle |
| 5,762,255 | A | 6/1998 | Chrisman et al. |
| 5,817,111 | A | 10/1998 | Riza |
| 6,508,830 | B2 | 1/2003 | Steiner |
| 6,544,281 | B2 | 4/2003 | ElAttrache et al. |
| 6,605,047 | B2 | 8/2003 | Zarins et al. |
| 6,991,636 | B2 | 1/2006 | Rose |
| 7,083,576 | B2 | 8/2006 | Zarins et al. |
| 7,329,272 | B2 | 2/2008 | Burkhart et al. |
| D566,272 | S | 4/2008 | Walburg et al. |
| 7,494,461 | B2 | 2/2009 | Wells et al. |
| D605,764 | S | 12/2009 | Griffis, III et al. |
| 7,662,160 | B2 | 2/2010 | Bojarski et al. |
| 7,780,055 | B2 | 8/2010 | Scirica et al. |
| 7,842,050 | B2 | 11/2010 | Diduch et al. |
| 7,879,046 | B2 | 2/2011 | Weinert et al. |
| 7,993,369 | B2 | 8/2011 | Dreyfuss |
| 8,114,128 | B2 | 2/2012 | Cauldwell et al. |
| 8,133,257 | B2 | 3/2012 | Cook et al. |
| 8,133,258 | B2 | 3/2012 | Foerster et al. |
| 8,317,829 | B2 | 11/2012 | Foerster et al. |
| 8,425,536 | B2 | 4/2013 | Foerster et al. |
| 8,430,909 | B2 | 4/2013 | Dreyfuss |
| 8,435,264 | B2 | 5/2013 | Sojka et al. |
| 8,469,983 | B2 | 6/2013 | Fung et al. |
| 8,556,970 | B2 | 10/2013 | Piccirillo |
| 8,808,313 | B2 | 8/2014 | Thorne et al. |
| 8,882,801 | B2 | 11/2014 | DiMatteo et al. |
| 9,034,001 | B2 | 5/2015 | Cheng et al. |
| 9,107,662 | B2 | 8/2015 | Kostrzewski |
| 9,113,859 | B2 | 8/2015 | Dooney, Jr. et al. |
| 9,179,907 | B2 | 11/2015 | ElAttrache et al. |
| 9,226,817 | B2 | 1/2016 | Dougherty et al. |
| 9,277,910 | B2 | 3/2016 | Nason et al. |
| 9,277,951 | B1 | 3/2016 | Hovis |
| 9,295,460 | B2 | 3/2016 | Hoof et al. |
| 9,370,351 | B2 | 6/2016 | Sojka et al. |
| 9,451,951 | B2 | 9/2016 | Sullivan et al. |
| 9,456,818 | B2 | 10/2016 | Torrie |
| 9,486,207 | B2 | 11/2016 | Dooney, Jr. et al. |
| 9,526,492 | B2 | 12/2016 | Lombardo et al. |
| 9,545,252 | B2 | 1/2017 | Howard et al. |
| 9,566,060 | B2 | 2/2017 | Dougherty et al. |
| 9,706,986 | B2 | 7/2017 | ElAttrache et al. |
| 9,717,587 | B2 | 8/2017 | Dougherty et al. |
| 9,763,655 | B2 | 9/2017 | Sengun |
| 9,770,240 | B2 | 9/2017 | Dougherty et al. |
| 9,775,599 | B2 | 10/2017 | ElAttrache et al. |
| 9,782,250 | B2 | 10/2017 | Dougherty et al. |
| 9,795,374 | B2 | 10/2017 | Dougherty et al. |
| 9,801,621 | B2 | 10/2017 | Benavitz |
| 9,801,629 | B2 | 10/2017 | Farascioni et al. |
| 9,808,240 | B2 | 11/2017 | Parsons et al. |
| 9,888,915 | B2 | 2/2018 | Torrie |
| 9,907,548 | B2 | 3/2018 | Dougherty et al. |
| 9,936,940 | B2 | 4/2018 | Palese et al. |
| 9,999,496 | B2 | 6/2018 | Dougherty et al. |
| 10,039,546 | B2 | 8/2018 | Williams et al. |
| 10,052,091 | B2 | 8/2018 | Dreyfuss et al. |
| 10,085,746 | B2 | 10/2018 | Fischvogt |
| 10,149,678 | B1 | 12/2018 | Martin et al. |
| 10,149,752 | B2 | 12/2018 | Dougherty et al. |
| 10,159,478 | B2 | 12/2018 | Howard et al. |
| D842,471 | S | 3/2019 | Alladu et al. |
| 10,238,377 | B2 | 3/2019 | Nason et al. |
| 10,265,062 | B2 | 4/2019 | Foerster et al. |
| 10,335,137 | B2 | 7/2019 | Arai et al. |
| 10,433,830 | B2 | 10/2019 | Sengun et al. |
| 10,512,454 | B2 | 12/2019 | Heneveld |
| 10,548,711 | B2 | 2/2020 | Dougherty et al. |
| 10,582,925 | B2 | 3/2020 | Marks et al. |
| 10,709,436 | B2 | 7/2020 | Burkhart et al. |
| 10,716,556 | B2 | 7/2020 | ElAttrache et al. |
| 10,888,312 | B2 | 1/2021 | Balboa et al. |
| D977,095 | S | 1/2023 | Shainwald et al. |
| 11,617,570 | B2 | 4/2023 | Lombardo et al. |
| D1,013,170 | S | 1/2024 | Kimball |
| D1,019,945 | S | 3/2024 | Jacobs et al. |
| D1,028,232 | S | 5/2024 | Shainwald et al. |
| 12,137,894 | B2 | 11/2024 | Jacobs et al. |
| 2001/0029376 | A1 | 10/2001 | Sater et al. |
| 2004/0082956 | A1 | 4/2004 | Baldwin et al. |
| 2004/0153074 | A1 | 8/2004 | Bojarski et al. |
| 2007/0219557 | A1 | 9/2007 | Bourque et al. |
| 2009/0076545 | A1 | 3/2009 | DiMatteo et al. |
| 2009/0248068 | A1 | 10/2009 | Lombardo et al. |
| 2011/0224726 | A1 | 9/2011 | Lombardo et al. |
| 2014/0243892 | A1 | 8/2014 | Choinski |
| 2014/0276987 | A1 | 9/2014 | Saliman |
| 2014/0364906 | A1 | 12/2014 | Palese et al. |
| 2015/0209026 | A1 | 7/2015 | Lanois et al. |
| 2016/0135801 | A1 | 5/2016 | Lombardo et al. |
| 2017/0000476 | A1 | 1/2017 | Dougherty et al. |
| 2017/0042533 | A1 | 2/2017 | Lunn et al. |
| 2017/0172562 | A1 | 6/2017 | Lombardo |
| 2017/0303912 | A1 | 10/2017 | ElAttrache et al. |
| 2017/0360427 | A1 | 12/2017 | Ziniti et al. |
| 2018/0235598 | A1 | 8/2018 | Burkhart et al. |
| 2018/0235599 | A1 | 8/2018 | Burkhart et al. |
| 2018/0256150 | A1 | 9/2018 | Gustafson et al. |
| 2018/0256152 | A1 | 9/2018 | Palese et al. |
| 2018/0338755 | A1 | 11/2018 | Palese et al. |
| 2019/0053888 | A1 | 2/2019 | Dougherty et al. |
| 2019/0090868 | A1 | 3/2019 | Bracy et al. |
| 2019/0159771 | A1 | 5/2019 | Balboa et al. |
| 2019/0159772 | A1 | 5/2019 | Norton et al. |
| 2019/0167252 | A1 | 6/2019 | Nason et al. |
| 2019/0290420 | A1 | 9/2019 | Dougherty et al. |
| 2019/0350577 | A1 | 11/2019 | Norton et al. |
| 2019/0380692 | A1 | 12/2019 | Brazil et al. |
| 2020/0008926 | A1 | 1/2020 | Power |
| 2020/0015809 | A1 | 1/2020 | Cauldwell et al. |
| 2020/0015816 | A1 | 1/2020 | Cauldwell et al. |
| 2020/0155137 | A1 | 5/2020 | Brunsvold et al. |
| 2020/0205805 | A1 | 7/2020 | Marks et al. |
| 2020/0253598 | A1 | 8/2020 | Holmes, Jr. |
| 2020/0383679 | A1 | 12/2020 | Alfia et al. |
| 2021/0338223 | A1 | 11/2021 | Patel et al. |
| 2021/0338224 | A1 | 11/2021 | Patel et al. |
| 2021/0338225 | A1 | 11/2021 | Patel et al. |
| 2023/0149009 | A1 | 5/2023 | Housman et al. |
| 2023/0210512 | A1 | 7/2023 | Jacobs et al. |
| 2024/0000445 | A1 | 1/2024 | Gabriel et al. |

FOREIGN PATENT DOCUMENTS

| | | | |
|---|---|---|---|
| WO | 2012177386 | A1 | 12/2012 |
| WO | 2019014557 | A1 | 1/2019 |

OTHER PUBLICATIONS

International Search Report and Written Opinion for PCT Application No. PCT/EP2022/088033 mailed Apr. 4, 2023.

MSC Industrial Supply Co., "Tech Essentials: Thread Forming Taps," dated no later than Apr. 10, 2021, available at <https://www.mscdirect.com/basicsof/thread-forming-taps> (1 page).

U.S. Appl. No. 17/565,514, filed Dec. 30, 2021, Jordan Jacobs et al.

U.S. Appl. No. 29/821,482, filed Dec. 30, 2021, Jordan N. Jacobs et al.

U.S. Appl. No. 29/929,377, filed Feb. 21, 2024, Jordan N. Jacobs et al.

KNOTLESS ANCHOR INSERTER TOOL EXTRACTION

CROSS REFERENCE TO RELATED APPLICATIONS

The present application is a continuation of U.S. patent application Ser. No. 17/565,514, now U.S. patent Ser. No. 12/137,894, entitled “filed Dec. 30, 2021”, which is hereby incorporated by reference in its entirety.

FIELD

The present disclosure generally relates to knotless anchor inserter tool extraction.

BACKGROUND

A variety of injuries and conditions require repair of soft tissue damage, or reattachment of soft tissue to bone and/or surrounding tissue. For example, when otherwise healthy tissue has been torn away from a bone, such as a labrum tearing away from a glenoid (shoulder instability), surgery is often required to reattach the tissue to the bone, to allow healing and a natural reattachment to occur. A number of devices and methods have been developed for performing these surgical repairs. Some of the more successful methods including the use of suture fixation members, such as suture anchors, which typically include an anchor body having a suture attachment feature and a tissue or bone engaging feature for retaining the suture anchor within or adjacent to the tissue or bone. Depending on the specific injury, one or more suture anchors connected to, or interconnected by, one or more segment of suture, may be used to perform the repair.

Surgery can also be required when a tear occurs in the substance of a single type of tissue. Sutures can also be used in conjunction with one or more suture anchors to repair such tissue tears. Sutures can be fastened to suture anchors and to tissue using knots tied by the surgeon during a repair procedure, or using “knotless” devices and methods, where one or more anchors and one or more sutures can be connected and tensioned without the surgeon needing to tie knots during the surgery. Knotless anchoring is of particular utility for minimally invasive surgeries, such as endoscopic or arthroscopic repairs, where the surgeon remotely manipulates the suture at the surgical site using tools inserted through a small diameter cannula, an endoscopic tube, or otherwise percutaneously, which can make the knotting process difficult and tedious. However, while knotless anchors can be very effective in reattaching soft tissue to bone, the small size of the anchor and patient anatomy can make it difficult to locate and insert the anchor into the bone hole. Additionally, visualization of the hole and the anchor can be difficult due to challenging angles and the tight nature of the joint space.

Accordingly, there remains a need for improved devices, systems, and methods for knotless anchor insertion.

SUMMARY

In general, devices, systems, and methods for knotless anchor inserter tool extraction are provided.

In one aspect, a surgical system is provided that in one embodiment includes an anchor and an inserter tool. The anchor is configured to be implanted in bone. The inserter tool includes an outer shaft, an inner shaft, and a retraction mechanism. The outer shaft is configured to push the anchor distally along a longitudinal axis of the inserter tool. The inner shaft is positioned in the outer shaft and in the anchor with a distal end of the inner shaft positioned distal to the outer shaft and the anchor. The distal end of the inner shaft is configured to releasably couple to a suture. The retraction mechanism is configured to be actuated to cause the inner shaft to move proximally relative to the outer shaft and the anchor along the longitudinal axis of the inserter tool.

The surgical system can vary in any number of ways. For example, the retraction mechanism can be configured as a lever. The retraction mechanism can include a lever handle operatively coupled to the inner shaft and configured to be moved relative to the outer shaft and the anchor and thereby cause the inner shaft to move proximally relative to the outer shaft and the anchor. The retraction mechanism can further include a lock configured to prevent the lever handle from being moved relative to the outer shaft and the anchor prior to the outer shaft pushing the anchor distally. The outer shaft pushing the anchor distally can be configured to move the lock from a locked position, in which the lock prevents the lever handle from being moved relative to the outer shaft and the anchor, to an unlocked position, in which the lock allows the lever handle to move relative to the outer shaft and the anchor. The retraction mechanism can also include a yoke fixedly attached to the inner shaft, and the lever handle being moved relative to the outer shaft and the anchor can also cause the yoke to move proximally relative to the outer shaft and the anchor.

For another example, the retraction mechanism can be configured as a rack and pinion mechanism.

For yet another example, the retraction mechanism can be configured as a lead screw mechanism.

For still another example, the retraction mechanism can include a lock configured to prevent the retraction mechanism from being actuated prior to the outer shaft pushing the anchor distally. The inserter tool can further include a locking mechanism configured to move from a locked position, in which the locking mechanism prevents the outer shaft from pushing the anchor distally, to an unlocked position, in which the locking mechanism allows the outer shaft to push the anchor distally.

For yet another example, the inserter tool can also include a handle including a holding mechanism configured to hold the outer shaft in position relative to the handle during the actuation of the retraction mechanism, and the inner shaft can also be caused by actuation of the retraction mechanism to move proximally relative to the handle. The outer shaft can be configured to move distally relative to the handle to push the anchor distally along the longitudinal axis of the inserter tool.

For another example, the inserter tool can further include a handle configured to be positioned outside of a body of a patient with the distal end of the inner shaft positioned in a hole in the bone, the outer shaft can extend distally from the handle, the inner shaft can extend distally from the handle, and the retraction mechanism can be configured to be positioned outside of the body of the patient with the distal end of the inner shaft positioned in the hole in the bone.

For still another example, the inserter tool can have an enclosed passage that is configured to seat a suture therethrough to releasably couple the inner shaft to the suture. The actuation of the retraction mechanism can be configured to cause a pliable member of the inserter tool to automatically unfold in response to the inner shaft moving proximally relative to the outer shaft and the anchor and thereby cause the enclosed passage to be opened. The surgical system can further include the suture seated through the enclosed passage. The suture can be seated through the enclosed passage prior to actuation of the retraction mechanism and prior to the distal end of the inner shaft being positioned in a hole in the bone and can be seated through the enclosed passage after the outer shaft pushes the anchor distally such that the anchor traps the suture between an exterior surface of the anchor and a wall of the hole in the bone. The pliable member can be integral with the inner shaft, or the pliable member can be a separate element attached to the inner shaft.

For yet another example, the distal end of the inner shaft can include a suture retention channel configured to seat the suture therethrough to releasably couple the inner shaft to the suture, and the suture retention channel can be configured to be positioned in a hole in the bone prior to the outer shaft pushing the anchor distally into the bone.

In another aspect, a surgical method is provided that in one embodiment includes positioning a distal end of an inner shaft of an inserter tool in a bone hole. The distal end of the inner shaft is releasably coupled to a suture such that the suture is also positioned in the bone hole. The surgical method also includes moving an outer shaft of the inserter tool axially and distally relative to the inner shaft, thereby causing an anchor to slide along the inner shaft and be positioned in the bone hole such that the anchor traps the suture between an exterior surface of the anchor and a wall of the bone hole. The surgical method also includes, after the movement of the outer shaft axially and distally, actuating a retraction mechanism of the inserter tool and thereby causing the inner shaft to move axially and proximally relative to the outer shaft and the anchor such that the inner shaft is removed from the bone hole and the anchor and the suture remain in the bone hole.

The surgical method can have any number of variations. For example, the retraction mechanism can be configured as a lever. The retraction mechanism can include a lever handle, the retraction mechanism can include a yoke fixedly attached to the inner shaft, and actuating the retraction mechanism can include moving the lever handle relative to the outer shaft and the anchor, thereby causing the yoke and the inner shaft to move proximally relative to the outer shaft and the anchor. The retraction mechanism can further include a lock that prevents the lever handle from being moved relative to the outer shaft and the anchor prior to the outer shaft pushing the anchor distally. The outer shaft pushing the anchor distally can cause the lock to move from a locked position, in which the lock prevents the lever handle from being moved relative to the outer shaft and the anchor, to an unlocked position, in which the lock allows the lever handle to move relative to the outer shaft and the anchor.

For another example, the retraction mechanism can be configured as a rack and pinion mechanism.

For yet another example, the retraction mechanism can be configured as a lead screw mechanism.

For still another example, before the movement of the outer shaft axially and distally, the inserter tool can have an enclosed passage in which the suture is seated, and the actuation of the retraction mechanism can also cause a pliable member of the inserter tool to move relative to the outer shaft and the anchor and to bend such that the enclosed passage opens. The pliable member can be integral with the inner shaft, or the pliable member can be a separate element attached to the inner shaft.

For another example, striking a strike cap of the inserter tool can cause the movement of the outer shaft axially and distally, and the striking of the strike cap can cause a lock of the retraction mechanism to move from a locked position, in which the lock prevents the retraction mechanism from being actuated, to an unlocked position, in which the lock allows the retraction mechanism to be actuated. A holding mechanism of a handle of the inserter tool can hold the outer shaft in position relative to the handle during the actuation of the retraction mechanism. The surgical method can also include moving a locking mechanism from a locked position, in which the locking mechanism prevents the outer shaft from moving axially and distally relative to the inner shaft, to an unlocked position, in which the locking mechanism allows the outer shaft to move axially and distally relative to the inner shaft.

For still another example, the inserter tool can include a handle that is positioned outside of a body of a patient with the distal end of the inner shaft positioned in the bone hole, the outer shaft can extend distally from the handle, the inner shaft can extend distally from the handle, and the retraction mechanism can be positioned outside of the body of the patient with the distal end of the inner shaft positioned in the bone hole.

In another embodiment, a surgical method includes positioning a distal end of an inner shaft of an inserter tool and positioning a pliable member of the inserter tool in a bone hole. The surgical method also includes moving an outer shaft of the inserter tool axially and distally relative to the inner shaft, thereby causing an anchor to move axially and distally and thereby be positioned in the bone hole such that the anchor traps the suture between an exterior surface of the anchor and a wall of the bone hole. The surgical method also includes, after the movement of the outer shaft axially and distally, actuating a retraction mechanism of the inserter tool and thereby causing the inner shaft and the pliable member to move axially and proximally relative to the outer shaft and the anchor such that the inner shaft and the pliable member are removed from the bone hole and the anchor and the suture remain in the bone hole. The pliable member unfolds during the axial and proximal movement of the pliable member.

The surgical method can vary in any number of ways. For example, the retraction mechanism can be configured as a lever. The retraction mechanism can include a lever handle, the retraction mechanism can include a yoke fixedly attached to the inner shaft, and actuating the retraction mechanism can include moving the lever handle relative to the outer shaft and the anchor, thereby causing the yoke and the inner shaft to move proximally relative to the outer shaft and the anchor. The retraction mechanism can further include a lock that prevents the lever handle from being moved relative to the outer shaft and the anchor prior to the outer shaft moving axially and distally relative to the inner shaft. The outer shaft moving axially and distally relative to the inner shaft can cause the lock to move from a locked position, in which the lock prevents the lever handle from being moved relative to the outer shaft and the anchor, to an unlocked position, in which the lock allows the lever handle to move relative to the outer shaft and the anchor.

For another example, the retraction mechanism can be configured as a rack and pinion mechanism.

For yet another example, the retraction mechanism can be configured as a lead screw mechanism.

For still another example, striking a strike cap of the inserter tool can cause the movement of the outer shaft axially and distally, and the striking of the strike cap can cause a lock of the retraction mechanism to move from a locked position, in which the lock prevents the retraction mechanism from being actuated, to an unlocked position, in which the lock allows the retraction mechanism to be actuated. A holding mechanism of a handle of the inserter tool can hold the outer shaft in position relative to the handle during the actuation of the retraction mechanism. The surgical method can also include moving a locking mechanism from a locked position, in which the locking mechanism prevents the outer shaft from moving axially and distally relative to the inner shaft, to an unlocked position, in which the locking mechanism allows the outer shaft to move axially and distally relative to the inner shaft.

For yet another example, the inserter tool can include a handle that is positioned outside of a body of a patient with the distal end of the inner shaft positioned in the bone hole, the outer shaft can extend distally from the handle, the inner shaft can extend distally from the handle, and the retraction mechanism can be positioned outside of the body of the patient with the distal end of the inner shaft positioned in the bone hole.

For still another example, the pliable member can be integral with the inner shaft, or the pliable member can be a separate element attached to the inner shaft.

BRIEF DESCRIPTION OF DRAWINGS

This disclosure will be more fully understood from the following detailed description taken in conjunction with the accompanying drawings, in which.

DETAILED DESCRIPTION

Figure 1:
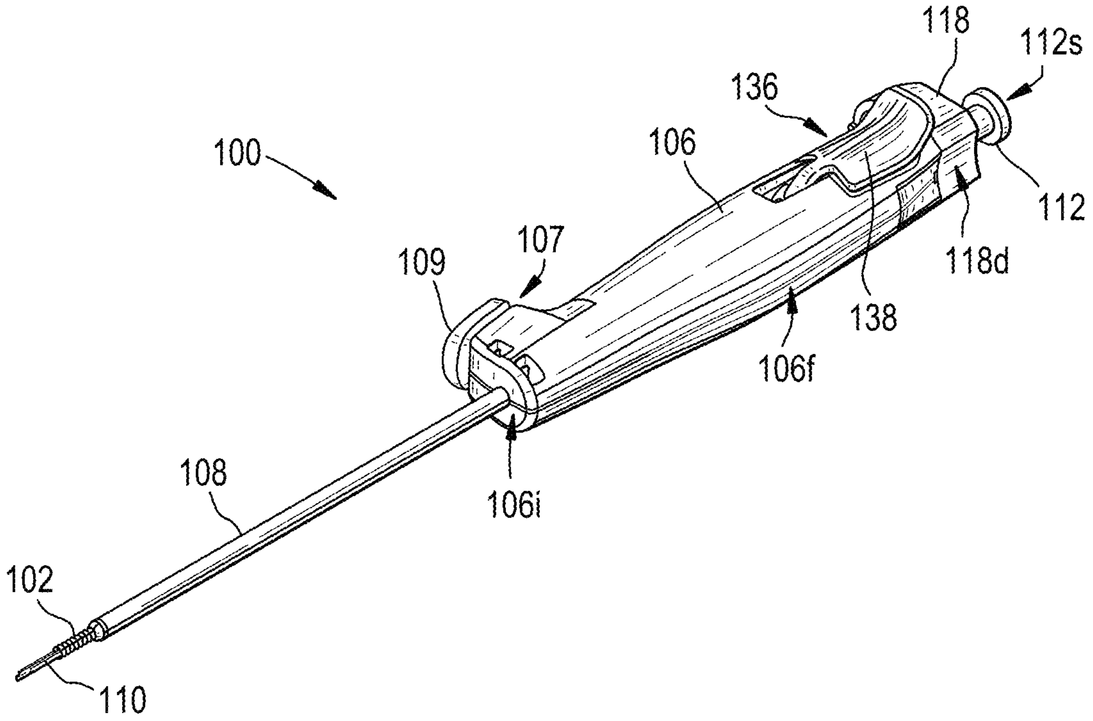
FIG. 1 is a perspective view of one embodiment of an inserter tool and one embodiment of an anchor releasably coupled to the inserter tool.
Figure 2:
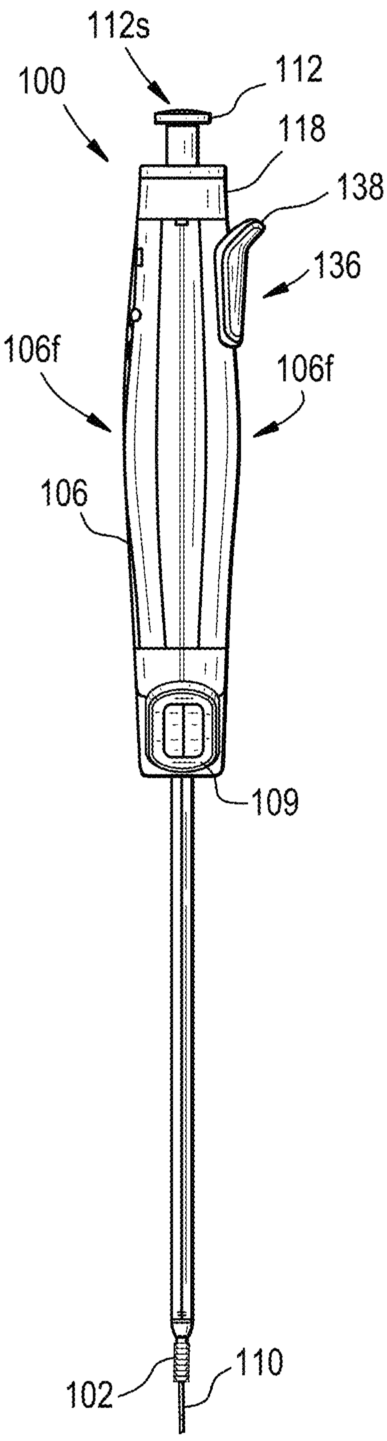
FIG. 2 is a side view of the inserter tool and the anchor of FIG. 1.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary devices, systems, and methods for knotless anchor inserter tool extraction are provided. In general, an inserter tool is configured for knotless anchor insertion in a soft tissue repair surgical procedure. The inserter tool is configured to insert an anchor into a bone of a patient to secure a soft tissue relative to the bone. A suture coupled to the soft tissue is secured relative to the bone by being trapped between an exterior surface of the anchor and a bone surface defining a hole in the bone in which the anchor is positioned. The anchor therefore allows the suture to be secured in position without needing to be knotted, which can be time consuming and/or difficult to perform during surgery because of small suture diameter, limited working area at a joint space, a wet surgical environment, and/or limited visualization at the surgical site due to challenging angles and the tight nature of the joint space.

The inserter tool is configured to have each of the suture and the anchor releasably coupled thereto and, with the suture and the anchor releasably coupled thereto, to insert each of the suture and the anchor into the bone hole. The inserter tool is configured to position the suture in the bone hole before the anchor is secured in the bone hole. The inserter tool is thus configured to allow the suture to be tensioned relative to the bone and the anchor after the suture has been positioned in the bone hole and before the anchor is secured in the bone hole to fix the suture in position relative to the bone, thereby allowing the soft tissue to be desirably positioned relative to the bone before being secured in position for healing. The inserter tool is configured to advance the anchor into the bone hole by longitudinally translating the anchor in a distal direction into the bone hole, such as by hitting the inserter tool with a mallet, hammer, or other tool, thereby trapping the suture between the exterior surface of the anchor and the bone surface defining the bone hole. After the anchor has been inserted into the bone, the inserter tool is configured to be removed from the patient's body with the anchor and the suture remaining in the bone.

With the anchor implanted in the bone and the suture fixed relative to the bone, a portion of the inserter tool is positioned within an inner lumen of the anchor. The anchor in the bone can exert a force on the portion of the inserter tool positioned within the anchor's inner lumen. The anchor may therefore act as a vise that tends to hold the inserter tool within the anchor's inner lumen. Additionally, a higher the density of the bone in which the anchor is implanted, the more force may be applied to the inserter tool. The force applied to the inserter tool by the anchor needs to be overcome to remove the inserter tool from within the anchor before the inserter tool can be removed from the patient's body. The inserter tool includes a retraction mechanism configured to cause the inserter tool to be removed from within the anchor. The retraction mechanism is configured to cause the portion of the inserter tool positioned within the anchor to longitudinally translate relative to the anchor along the longitudinal axis of the inserter tool, which is coaxial with a longitudinal axis of the anchor. The longitudinal translation of the inserter tool is in a proximal direction, as opposed to a distal direction in which the inserter tool was advanced into the patient to the bone and in which the anchor was driven into bone, such that the inserter tool is being retracted. The retraction mechanism thus provides a mechanical mechanism to remove the inserter tool from within the implanted anchor, thereby relieving a user from having to manually apply longitudinal force to the inserter tool for the removal from within the anchor and relieving accordant user concern that too much longitudinal force is being applied such that the anchor and/or the suture may be loosened or removed from the bone. Removing the inserter tool from within the anchor by longitudinally translating the inserter tool along the longitudinal axis of the inserter tool, and the longitudinal axis of the anchor, may be less time consuming and/or may require less user-applied force than other methods of decoupling a tool from an implanted anchor that include rotating the tool about its longitudinal axis. Unlike longitudinally translating the inserter tool for removal, rotating the tool for removal can risk rotating the anchor and/or unintended off axis loading, which can cause the anchor to become less securely positioned in the bone and/or can cause damage to the suture and/or to the anchor.

The retraction mechanism is located in a proximal portion of the inserter tool that is typically located entirely outside of a patient's body during use of the inserter tool in a surgical procedure. Conversely, the portion of the inserter tool positioned within the anchor after the anchor has been inserted into the bone is located in a distal portion of the inserter tool that is located entirely inside the patient's body during the surgical procedure. The retraction mechanism being located in the proximal portion of the inserter tool may provide a mechanical advantage by the removal force applied by the retraction mechanism to the portion of the inserter tool positioned within the anchor being applied a distance away from the portion of the inserter tool positioned within the anchor.

It may be difficult to visualize the anchor implanted in the bone due to the anchor being positioned sub-flush to the bone, challenging angles, and/or the tight nature of the joint space. Even if the implanted anchor can be visualized, it may be impossible to visualize the portion of the inserter tool positioned within the anchor due to obstruction by the bone, the anchor, a portion of the inserter tool located outside of the anchor and outside of the bone, and/or other matter located outside of the anchor and outside of the bone. It may therefore be impossible for a user to visually confirm that the inserter tool has been removed from within the anchor because the anchor, the inserter tool, or both the anchor and the inserter tool may not be able to be fully or even partially visualized within the patient's body. The retraction mechanism located in the proximal portion of the inserter tool is visible by the user, as the retraction mechanism is located outside of the patient's body, and may thus allow the user to visually confirm that the inserter tool has been removed from within the anchor even if the user cannot visualize the anchor and/or the inserter tool within the patient's body. As discussed further below, the retraction mechanism is configured to move from an initial, unactuated position to an actuated position to remove the inserter tool from within the anchor. The retraction mechanism being in the actuated position visually indicates to the user that the inserter tool has been removed from within the anchor.

The suture is releasably coupled to the inserter tool before the inserter tool is advanced into the patient's body. The inserter tool includes a suture retention channel configured to seat the suture therein. The suture retention channel is located distal to the anchor releasably coupled to the inserter tool. The suture seated in the suture retention channel can thus be positioned in the bone hole distal to the anchor, thereby allowing the anchor to be advanced distally into the bone hole with the suture already positioned in the bone hole. In an exemplary embodiment, the suture has a U-shape before and after the anchor is fixed in the bone hole. In the U-shape, each of the suture's legs extend longitudinally along opposed sides of the anchor, and an intermediate portion of the suture that connects the legs extends along the anchor's distal tip so as to loop around the anchor's distal tip. The U-shape configuration of the suture relative to the anchor may maximize a length of the suture that the anchor presses against to fix the suture in position relative to the bone, which may help ensure that the soft tissue coupled to the suture remains in a fixed position relative to the bone to facilitate healing.

The retraction of the inserter tool from within the anchor using the retraction mechanism does not interfere with the suture after the anchor and suture have been fixed in the bone hole. With the anchor and suture fixed in the bone hole, each of the suture's legs extends longitudinally along opposed sides of the anchor and proximally out of the bone hole, and the inserter tool extends longitudinally out of the anchor between the suture's legs. Longitudinal proximal movement of the portion of the inserter tool within the anchor to be removed from within the anchor therefore does not interfere with the suture, which is positioned on opposite sides of the inserter tool and thus can stay fixed relative to the anchor and the bone as desired before, during, and after retraction of the inserter tool.

The systems, devices, and methods described herein have applicability in a variety of surgical procedures for soft tissue repair, such as in a tissue repair surgical procedure at a joint such as a shoulder, a knee, or a hip.

Figure 6:
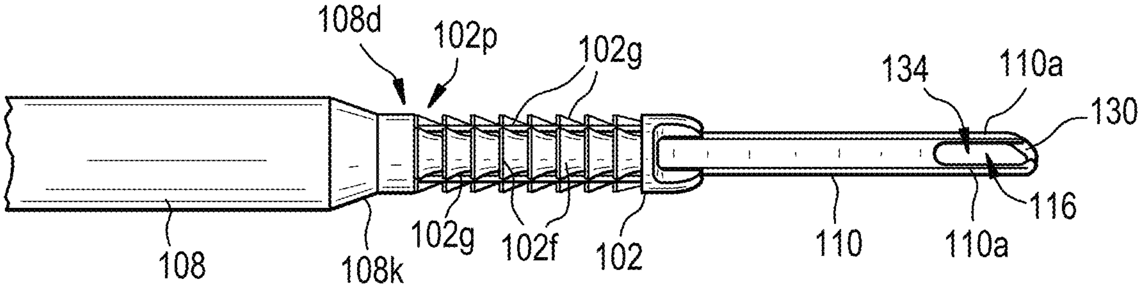
FIG. 6 is a side view of a distal portion of the inserter tool and the anchor of FIG. 1.
Figure 7:
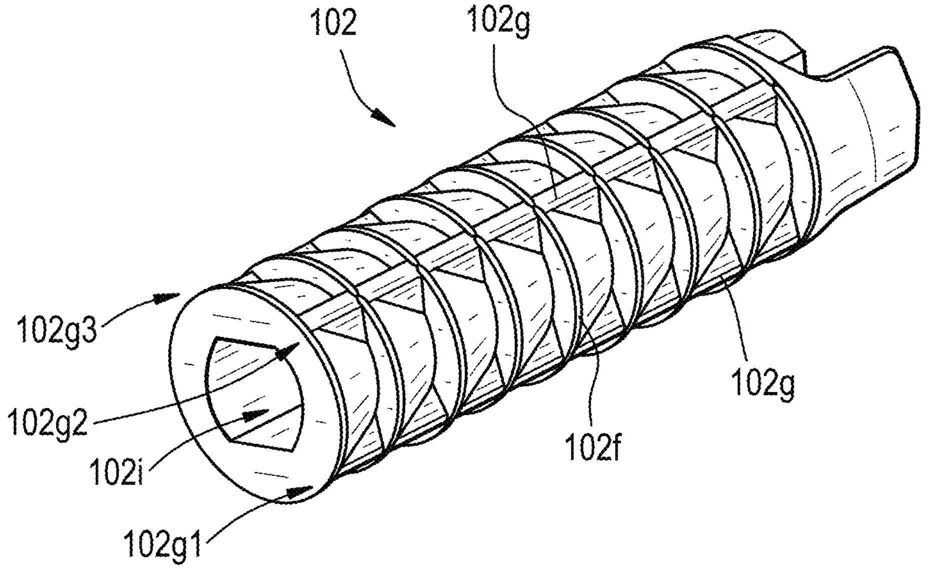
FIG. 7 is a perspective view of the anchor of FIG. 1.

FIGS. 1-5 illustrate one embodiment of an inserter tool 100, also referred to herein as an "inserter," for knotless anchor insertion in a soft tissue repair surgical procedure. In general, the inserter tool 100 is configured to insert an anchor 102 into a bone of a patient to secure a soft tissue relative to the bone. As shown in FIGS. 6 and 7, an inner lumen 102*i* extends through the anchor 102 such that the anchor 102 is cannulated. FIGS. 1-6 show the anchor 102 releasably coupled to the inserter tool 100. FIG. 7 shows the anchor 102 as a standalone element. A plurality of bone-engaging surface features 102*f* are formed on an exterior surface of the anchor 102. The bone-engaging surface features 102*f* are configured to engage bone to retain the anchor 102 in the bone, e.g., to engage a surface of bone defining a hole in bone in which the anchor 102 is positioned. The bone-engaging surface features 102*f* include a plurality of ribs each extending circumferentially around the anchor 102 at different axial positions along the anchor's longitudinal length. The bone-engaging surface features 102*f* can, however, have another configuration, such as a plurality of barbs or other form of protrusions formed on the anchor's exterior surface. The bone-engaging surface features 102*f* are also configured to engage a suture against the bone to help secure the suture relative to the bone.

The anchor 102 in this illustrated embodiment includes a plurality of gussets 102*g* that are configured to reinforce the anchor 102. The gussets 102*g* each extend longitudinally along the anchor 102. As shown in FIG. 7, a first set of the gussets 102*g*1 are aligned with one another along the anchor's length, a second set of the gussets 102*g*2 are aligned with one another along the anchor's length, a third set of the gussets 102*g*3 are aligned with one another along the anchor's length, and a fourth set of the gussets 102*g* are aligned with one another along the anchor's length. The fourth set of gussets 102*g* is obscured in FIG. 7. The first, second, third, and fourth sets of gussets 102*g* are arranged equidistantly around the circumference of the anchor 102, which may help reinforce the anchor 102 around the entire circumference thereof. In other embodiments, an anchor can include a different number of sets of gussets and/or the sets of gussets can be non-equidistantly arranged around the anchor's circumference.

The anchor 102 can be absorbable or non-absorbable. The anchor 102 can be made from any of a variety of materials, e.g., Polyether ether ketone (PEEK), Polylactic acid or polylactide (PLA), BIOCRYL®, BIOCRYL® RAPIDE®, titanium, ceramics, carbon fiber, stainless steel, etc. The anchor 102 can be formed by a variety of techniques, for example by machining, molding, metal injection molding, overmolding, or by a post-molding process such as post-molding machining. Exemplary embodiments of anchors include the Healix Advance™ anchors and the Gryphon® anchor available from DePuy Mitek, Inc. of Raynham, MA, and various exemplary embodiments of anchors and features thereof are further described in U.S. Pat. Pub. No. 2021/0338223 entitled "Knotless Anchor Insertion" published Nov. 4, 2021, U.S. Pat. No. 8,114,128 entitled "Cannulated Suture Anchor" issued Feb. 14, 2012, U.S. Pat. No. 8,882, 801 entitled "Dual Thread Cannulated Suture Anchor" issued Nov. 11, 2014, and U.S. Pat. No. 8,133,257 entitled "Bioabsorbable Suture Anchor System For Use In Small Joints" issued Mar. 13, 2012, which are hereby incorporated by reference in their entireties.

The inserter tool 100 includes a handle 106, an outer shaft 108 (also referred to herein as a "push tube") that extends distally from the handle 106, an inner shaft 110 that extends distally from the handle 106, and a strike cap 112 that extends proximally from the handle 106. The handle 106 is configured to be held by hand during use of the inserter 100. In robotic surgical implementations, the handle 106 can be held by a mechanical member of the robotic surgical system. The handle 106 has a generally cylindrical, distally-tapering shape in this illustrated embodiment but can have any of a variety of shapes.

Figure 8:
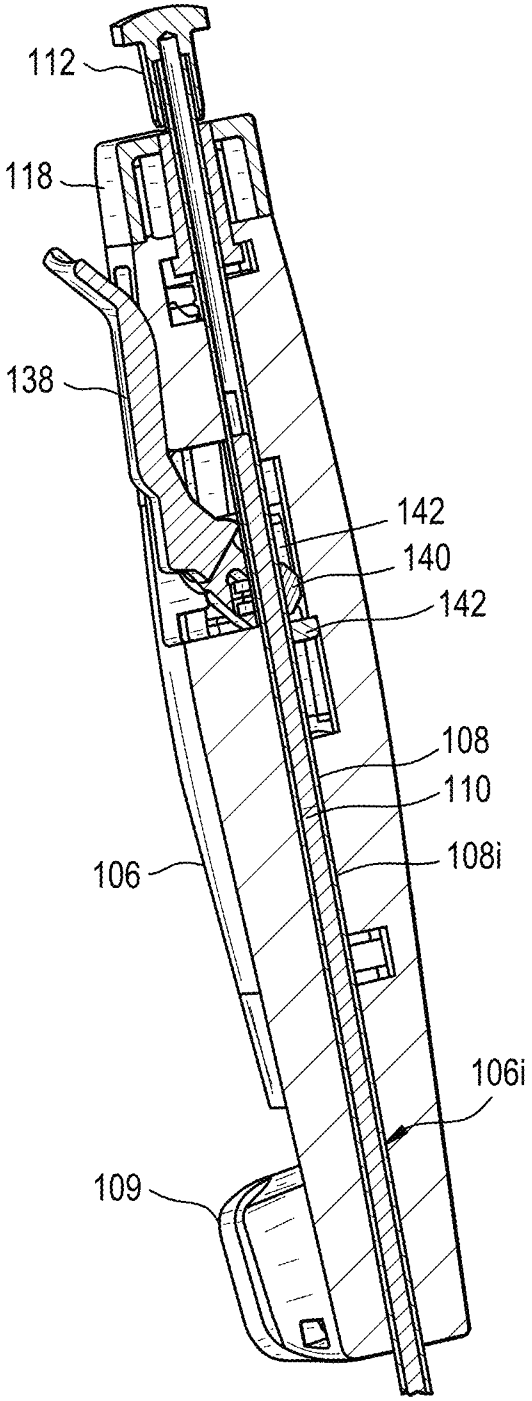
FIG. 8 is a cross-sectional view of a proximal portion of the inserter tool of FIG. 1.

As shown in FIGS. 1 and 8, the handle 106 has an inner lumen **106*i* extending therethrough. The outer and inner shafts 108, 110 are positioned in the handle's inner lumen 106*i* and extend distally out of the handle's inner lumen 106*i*. Proximal ends of one or both of the outer and inner shafts 108, 110 can be located within the handle's inner lumen 106*i*, or one or both of the outer and inner shafts 108, 110 can extend proximally beyond the handle 106 such that the respective proximal ends of the outer and inner shafts 108, 110 are located proximal to the handle 106. For example, as in this illustrated embodiment, the proximal end of the inner shaft 110 can be located within the inner lumen 106*i* of the handle 106, and the proximal end of the outer shaft 108 can extend proximally beyond the handle 106 and be located in the strike cap 112. For another example, the proximal end of the inner shaft 110 and the proximal end of the outer shaft 108 can be located within the inner lumen 106*i* of the handle 106**.

The handle 106 in this illustrated embodiment includes facets **106*f* on opposed sides, e.g., left and right sides, thereof. The facets 106*f*** are configured to help a user with grip and fine motor movements.

The handle 106 in this illustrated embodiment includes a suture retention member configured to releasably retain a suture to hold the suture in a desired position at a desired tension. A suture is traditionally retained using a hemostat. The inserter tool 100 including a suture retention member may eliminate the need to use any hemostats for the suture. The suture retention member is located at a distal end of the handle 106 but can be located elsewhere. Various embodiments of suture retention mechanisms are further described, for example, in previously mentioned U.S. Pat. Pub. No. 2021/0338223 entitled "Knotless Anchor Insertion" published Nov. 4, 2021.

The suture retention member in this illustrated embodiment includes a groove 107 on a side of the handle 106. The inserter 100 includes a single suture retention member in this illustrated embodiment but can include a plurality of suture retention mechanisms, such as first and second suture retention members on opposed sides of the handle 106. The groove 107 is defined between the handle 106 and an elastomeric cleat 109 fixedly attached to the handle 106. The elastomeric cleat 109 is made from an elastomeric material, such as rubber or other polymer. The handle 106 is made from a rigid, non-elastomeric material, such as a plastic such as polycarbonate or other plastic; metal (e.g., stainless steel, titanium, etc.); polytetrafluoroethylene (PTFE); or other biocompatible material. The groove 107 is thus located at a junction between an elastomeric material and a rigid material. The elastomeric material of the elastomeric cleat 109 allows a width of the groove 107 to dynamically increase to adjust to a size and shape of the suture being seated therein to securely hold the suture in the groove 107, gripped between the elastomeric material and the rigid material. The suture retention member is thus self-adjusting. Different sutures have different sizes and shapes, and the elastomeric cleat 109 is configured to dynamically adjust to the particular size and shape of a suture being seated therein. The suture being securely held in the groove 107 may help the suture's tension be maintained, e.g., without being lessened, while the suture is retained by the suture retention member. When the suture is released from the groove 107, the elastomeric cleat 109 is no longer gripping the suture and is thus allowed to return to its original, smaller width as the elastomeric material elastically returns to its original configuration.

A proximal surface of the handle 106 and a proximal surface of the elastomeric cleat 109 extends radially outward and tapers distally. The tapering is configured to urge a suture along the proximal surface of the handle 106 toward the elastomeric cleat 109 for seating the groove 107. The elastomeric cleat 109 has a beveled edge facing the groove 107, which may also help urge the suture into the groove 107.

As shown in FIG. 8, an inner lumen **108*i* extends through the outer shaft 108 such that the outer shaft 108 is cannulated. In an initial configuration of the inserter 100, which is shown in FIGS. 1-6 and 8, the inner shaft 110 is seated in the inner lumen 102*i* of the anchor 102 and in the inner lumen 108*i* of the outer shaft 108. As discussed further below, the inner shaft 110 is configured to be movable relative to the anchor 102 and to the outer shaft 108 to facilitate inner shaft 110 retraction, and the anchor 102 and the outer shaft 108 are each configured to be movable relative to the inner shaft 110 to facilitate delivery of the anchor 102 into a bone hole. In other embodiments, the outer shaft 108 is not cannulated and instead has an inner bore having an open distal end and a closed proximal end and in which the inner shaft 110** is configured to be movably seated.

A distal end **108*d* of the outer shaft 108 is located proximal to a proximal end 102*p* of the anchor 102. In an exemplary embodiment, as shown in FIG. 6, the outer shaft's distal end 108*d* abuts the anchor's proximal end 102*p* in the inserter's initial configuration, which may maximize transmission of a distal force applied to the outer shaft 108 to the anchor 102 and thereby help efficiently distally advance the anchor 102 into a bone hole. However, the outer shaft's distal end 108*d* can be spaced a distance proximal to the anchor's proximal end 102*p* in the inserter's initial configuration. The outer shaft 108 includes a distal knob 108*k* (also referred to herein as a "bushing") that tapers distally and defines the distal end 108*d* of the outer shaft 108. The distal tapering of the bushing 108*k* allows a proximal portion of the outer shaft 108 to have a larger diameter than the distal end 108*d* of the outer shaft 108 such that the smaller diameter at the distal end 108*d* of the outer shaft 108 corresponds to a diameter of the anchor 102 at its proximal end 102*p*, which may help the outer shaft 108 efficiently apply distally-directed force to the anchor 102**.

The strike cap 112 is configured to be struck with a mallet, hammer, or other tool on a proximal surface **112*s* thereof. The proximal surface 112*s* in this illustrated embodiment is convex curved, which may provide more feedback (compared to a flat surface) to a user striking the strike cap 112. The strike cap 112 can, however, have a flat surface, which may facilitate an even strike on the strike cap 112 and thus an evenly transmitted distal force from the strike cap 112 to the push tube 108. The proximal surface 112*s*** can however, have another shape, e.g., textured with ribs, raised dome protrusions, etc.; convex; etc.

The proximal surface 112*s* of the strike cap 112 is exposed for striking by a mallet, hammer, or other tool. In other embodiments, an inserter tool can include a strike cap and a protective member configured to cover or hide at least the strike surface of the strike cap. The protective member may help prevent premature striking of the strike cap and/or any unintentional distal movement of the strike cap and thus any unintentional distal advancement of an anchor coupled to the inserter tool. In some embodiments the protective member can completely cover or hide the strike cap. Various embodiments of protective members are further described, for example, in previously mentioned U.S. Pat. Pub. No. 2021/0338223 entitled "Knotless Anchor Insertion" published Nov. 4, 2021.

The inserter tool 100 includes a locking mechanism 118 configured to lock the outer shaft 108 in position relative to the inner shaft 110 when the locking mechanism 118 is in a locked position. FIGS. 3, 8, 9, and 11 show the locking mechanism 118 in the locked position. FIGS. 1, 2, 4, 5, 10, and 12 show the locking mechanism 118 in an unlocked position, in which the outer shaft 108 is not locked in position relative to the inner shaft 110. The locking mechanism 118 is configured to move from the locked position to the unlocked position by sliding relative to the outer shaft 108, the inner shaft 110, the strike cap 112, and the handle 106. The sliding movement of the locking mechanism 118 is lateral movement substantially perpendicular to coaxial longitudinal axes of the outer and inner shafts 108, 110. A person skilled in the art will appreciate that axes or other features may not be precisely perpendicular but nevertheless considered to be substantially perpendicular for any of one or more reasons, such as manufacturing tolerances or sensitivity of measurement equipment. The initial position of the locking mechanism 118 is the locked position, to help prevent premature distal translation of the outer shaft 108 relative to the inner shaft 110 and thus help prevent premature distal advancement of the anchor 102 relative to the inner shaft 110.

The locking mechanism 118 includes a depression 118*d* on a side thereof. The depression 118*d* is configured to communicate where a finger should be placed on the locking mechanism 118. The depression's surface is configured as a push surface on which a finger can be placed to push the locking mechanism 118 from the locked position to the unlocked position. A curvature of the depression 118*d* matches a curvature of the handle 106 adjacent to the locking mechanism 118 in the unlocked position. The matching curvature of the depression 118*d* and the handle 106 is configured to indicate to a user that the locking mechanism 118 has fully moved to the unlocked position.

Figure 9:
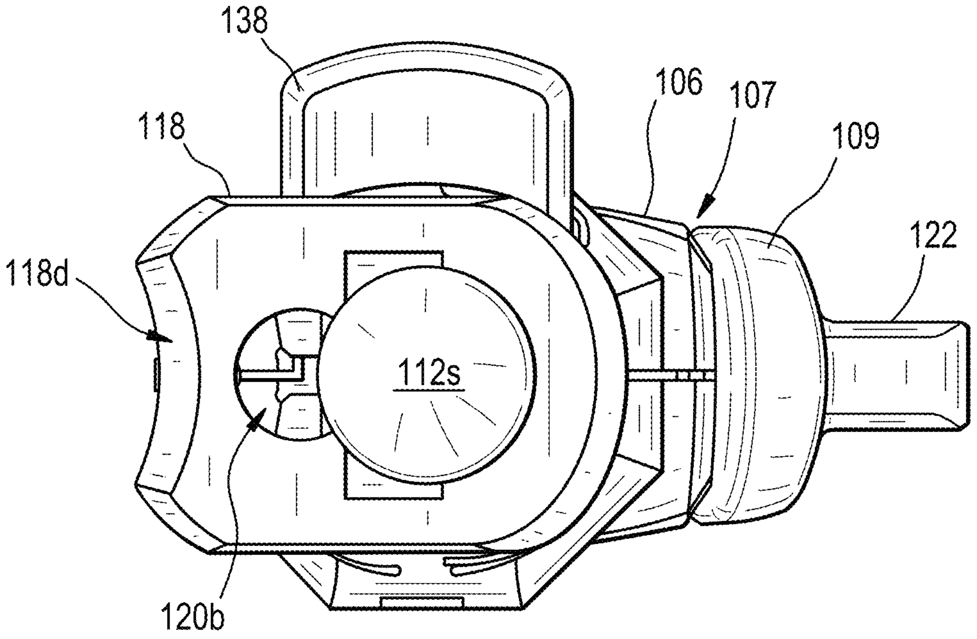
FIG. 9 is a proximal end view of the inserter tool and the loading aid of FIG. 3.
Figure 10:
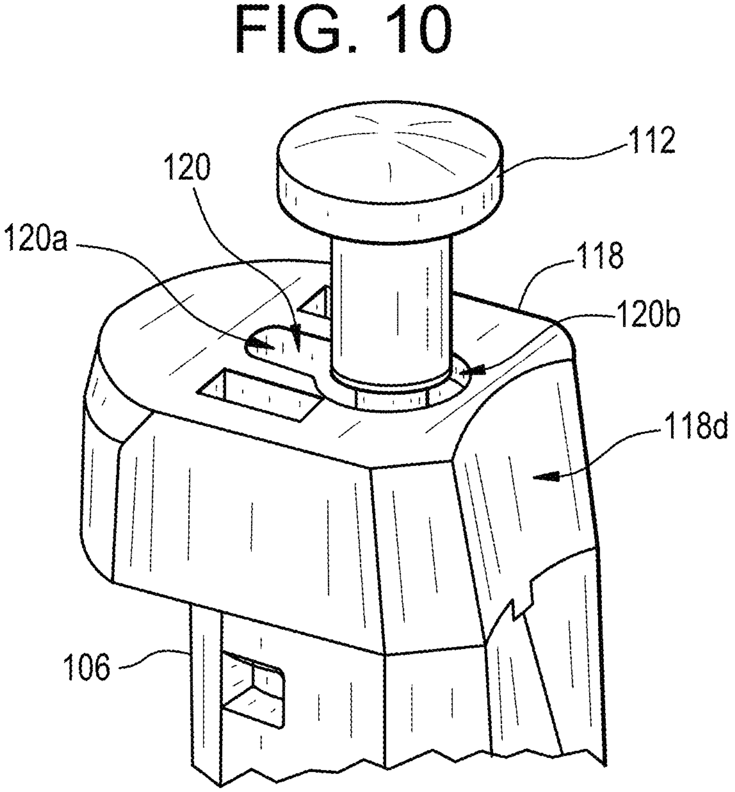
FIG. 10 is a perspective view of a proximal portion of the inserter tool of FIG. 1 with a locking mechanism of the inserter tool in an unlocked position before striking of a strike cap of the inserter tool.
Figure 11:
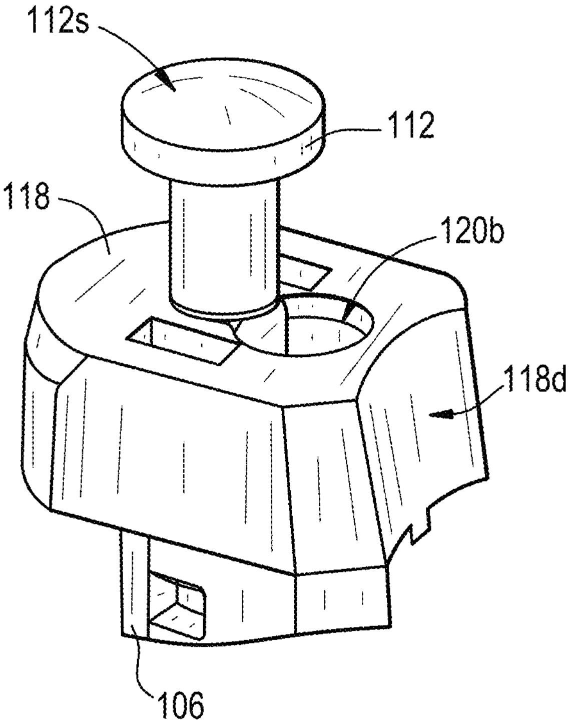
FIG. 11 is a perspective view of a proximal portion of the inserter tool of FIG. 1 with the locking mechanism of the inserter tool in a locked position.
Figure 12:
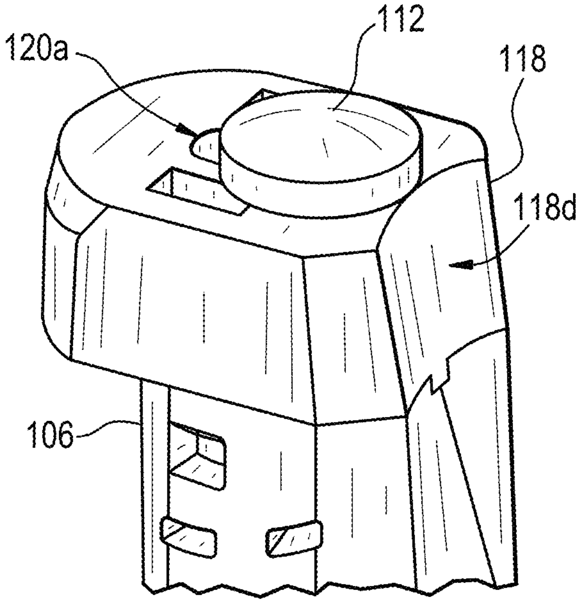
FIG. 12 is a perspective view of a proximal portion of the inserter tool of FIG. 10 after striking of the strike cap.

As shown in FIGS. 9-12, the locking mechanism 118 includes a keyhole 120 formed therein in which the strike cap 112 is configured to move. In embodiments in which the outer shaft 108 extends proximally from the handle 106 and into the strike cap 112, as in this illustrated embodiment as shown in FIG. 9, the outer shaft 108 is also configured move in the keyhole 120. The keyhole 120 includes a reduced diameter portion 120*a* and an enlarged diameter portion 120*b*. With the locking mechanism 118 in the locked position, the strike cap 112 is located proximal to the keyhole 120. The diameter of the reduced diameter portion 120*a* is less than a diameter of the strike cap 112 at least at the distal end of the strike cap 112. The strike cap 112 thus cannot move distally into the keyhole 120, thereby preventing the outer shaft 108 from moving distally by the strike cap 112 being struck on its proximal surface 112*s*. With the locking mechanism 118 in the unlocked position, the strike cap 112 is also located proximal to the keyhole 120. The diameter of the enlarged diameter portion 120*b* is greater than the diameter of the strike cap 112 at least at the distal end of the strike cap 112. The strike cap 112 thus can move distally into the keyhole 120, thereby allowing the outer shaft 108 to move distally by the strike cap 112 being struck on its proximal surface 112*s*. The diameter of the enlarged diameter portion 120*b* is less than a diameter of a head of the strike cap 112 that includes the proximal surface 112*s*, thereby preventing the strike cap 112 from fully passing into the keyhole 120 because a distal surface of the strike cap 112 will abut the locking mechanism 118 around the keyhole 120. FIG. 12 shows the locking mechanism 118 in the unlocked position after the strike cap 112 has been struck with the distal surface of the strike cap 112 abutting the locking mechanism 118 around the keyhole 120.

The locking mechanism 118 in this illustrated embodiment is not releasable from the inserter tool 100. In other embodiments, a locking mechanism is releasable from the inserter tool 100. Various embodiments of locking mechanisms are further described, for example, in previously mentioned U.S. Pat. Pub. No. 2021/0338223 entitled "Knotless Anchor Insertion" published Nov. 4, 2021.

As shown in FIG. 6, the inner shaft 110 includes a notch formed therein that defines a suture retention channel 116. The notch is formed in a distal end of the inner shaft 110 and is defined by distal arms 110*a* of the inner shaft 110. The suture retention channel 116 is configured to seat a suture therein. The suture retention channel 116 is configured to receive the suture therein through an open distal end of the suture retention channel 116. The suture retention channel 116 has a substantially constant diameter in this illustrated embodiment but can have different diameters in different portions, e.g., a proximal portion of the suture retention channel 116 having a greater diameter than a distal portion of the suture retention channel 116, a distal portion of the suture retention channel 116 having a greater diameter than a proximal portion of the suture retention channel 116, or other different diameters. A person skilled in the art will appreciate that values, such as diameter values, may not be precisely the same but nevertheless considered to be substantially the same for any of one or more reasons, such as manufacturing tolerances or sensitivity of measurement equipment.

The suture retention channel 116 may allow for more sutures and/or larger diameter suture(s) to be coupled to the inserter 100 than with other types of inserter tools since the suture(s) do not need to be folded over to be inserted into an aperture, eyelet, or other opening to be coupled to the inserter tool or to the anchor.

As shown in FIG. 6, the suture retention channel 116 is located distal to the anchor 102 releasably coupled to the inserter tool 100. The suture seated in the suture retention channel 116 can thus be positioned in the bone hole distal to the anchor 102, thereby allowing the anchor 102 to be advanced distally into the bone hole with the suture already positioned in the bone hole.

In this illustrated embodiment, as shown in FIG. 6, the inserter tool 100 includes a pliable member 130 (also referred to herein as a "flexible member"). The pliable member 130 is located distal to the anchor 102 that has the inner shaft 110 positioned in an inner lumen thereof. The pliable member 130 is configured to fold or bend without breaking, cracking, or otherwise losing structural integrity. The pliable member 130 has a free end configured to move relative to the inner shaft 110 such that the pliable member 130 can fold or bend relative to the inner shaft 110 to facilitate release of a suture from within the suture retention channel 116, as discussed further below. The pliable member 130 in this illustrated embodiment is a metal extension finger fixedly attached to the inner shaft 110 but can have other configurations, e.g., a metal single filament wire, a metal multi-filament wire, a braided fabric, a textile strand, a monofilament fiber, etc. Various embodiments of pliable members are further described, for example, in previously mentioned U.S. Pat. Pub. No. 2021/0338223 entitled "Knotless Anchor Insertion" published Nov. 4, 2021.

The pliable member 130 defines an enclosed passage 134 in cooperation with a distal end of the inner shaft 110 including the suture retention channel 116. The distal arms 110*a* of the inner shaft 110 thus define a portion of the enclosed passage 134. The pliable member 130 defines a distal end of the enclosed passage 134. A suture is configured to extend through the suture retention channel 116 and the enclosed passage 134 during use of the inserter tool 100, as discussed further below. The pliable member 130 is configured to move to open the enclosed passage 134 and thereby allow release of the suture from the suture retention channel 116, as also discussed further below. In general, the pliable member 130 is configured to flex to open the enclosed passage 134 by no longer providing a distal end of the enclosed passage 134.

In an exemplary embodiment, the pliable member 130 is made from a shape memory or superelastic material, such as Nitinol or other material, which may facilitate movement of the pliable member 134 between a resting configuration, shown in FIG. 6, and a bent configuration. The default configuration of the pliable member 130 is the resting configuration in which the enclosed passage 134 exists. The enclosed passage 134 does not exist with the pliable member 130 in the bent configuration. The pliable member 130 being in the resting configuration by default may help ensure that the suture remains seated in the suture retention channel 116 until desired.

The suture is positioned in the suture retention channel 116 and thus in the enclosed passage 134 by a user of the inserter tool 100, which may provide a user of the inserter 100 flexibility in deciding on a size and type of suture to use that is appropriate for a particular patient and a particular surgical procedure. The suture can be positioned in the suture retention channel 116 and the enclosed passage 134 by the user by hand, similar to the threading of a needle. Alternatively to hand positioning, the suture can be positioned in the suture retention channel 116 and the enclosed passage 134 using a tool such as a pusher tube or a loading aid. One embodiment of a loading aid 122 is illustrated in FIGS. 3-5 and 9 (the loading aid 122 is only partially shown in FIG. 5).

The loading aid 122 is shown releasably attached to the inserter tool 100 in FIGS. 3-5 and 9 before a suture is positioned in the suture retention channel 116 and the enclosed passage 134. In an exemplary embodiment, the loading aid 122 is pre-loaded on the inserter tool 100 during manufacturing, which may help ensure that the loading aid 122 is positioned correctly on the inserter 100 and/or may provide a reminder to a user of the inserter 100 that the suture should be coupled to the inserter 100 before the inserter 100 is advanced into a patient's body. Alternatively, the loading aid 122 can be loaded onto the inserter tool 100 by a user, which may allow for the inserter 100 to be sold without the loading aid 122 and thus at a lower cost than the inserter 100 sold with the loading aid 122.

The loading aid 122 in this illustrated embodiment includes a suture threader. A suture threader can have a variety of configurations, as will be appreciated by a person skilled in the art. In this illustrated embodiment, the loading aid 122 includes a base 124 and a wire loop 126 that is attached to the base 124 and that defines an enclosed passage 128. The base 124 of the loading aid 122 includes a plurality of clips 122*c* configured to releasably clip to the outer shaft 108 to releasably attach the loading aid 122 to the inserter tool 100. A suture is configured to be seated in the passage 128 defined by the loop 126. With the suture extending through the loop 126 of the loading aid 122, the loading aid 122 can be pulled by the base 124 in the direction of an arrow 124*a* on the base 124, e.g., printed thereon, etched therein, adhered thereon as a sticker, etc., to release the clips 122*c* from the outer shaft 108 and to pull the suture through the enclosed passage 134 defined by the inner shaft 110 and the suture retainer 132 so as to thread the suture through the enclosed passage 134 and the suture retention channel 116. The suture extending through the enclosed passage 134 and the suture retention channel 116 can thus be releasably coupled to the inserter tool 100 and have a U-shape with the inserter tool 100 in its initial configuration.

The inserter tool 100 includes a retraction mechanism 136 configured to cause the inserter tool 100 to be removed from within the anchor 102. The retraction mechanism 136 is configured to be actuated to cause a portion of the inserter tool 100 that is positioned within the anchor 102 to translate longitudinally and proximally relative to the anchor 102 and thus exit the anchor 102 through the anchor's open proximal end. As discussed further below, a distal portion of the inner shaft 110 of the inserter tool 100 is positioned within the anchor 102, e.g., within the inner lumen 102*i* thereof, after the anchor 102 has been advanced into a bone hole. The retraction mechanism 136 is thus configured to cause the inner shaft 110 to be extracted from within the anchor 102 by moving the inner shaft 110 proximally relative to the anchor 102. As discussed above, the suture retainer 132 is fixedly attached to the inner shaft 110 in the distal portion of the inner shaft 110. The retraction mechanism 136 is thus also configured to retract the suture retainer 132 proximally with the inner shaft 110. A suture seated in the enclosed passage 134 defined by the inner shaft 110 and the suture retainer 132 is not retracted with the inner shaft 110 and the suture retainer 132, as discussed further below. The anchor 102 and the suture coupled thereto can thus remain fixed to bone during and after the actuation of the retraction mechanism 136.

Figure 31:
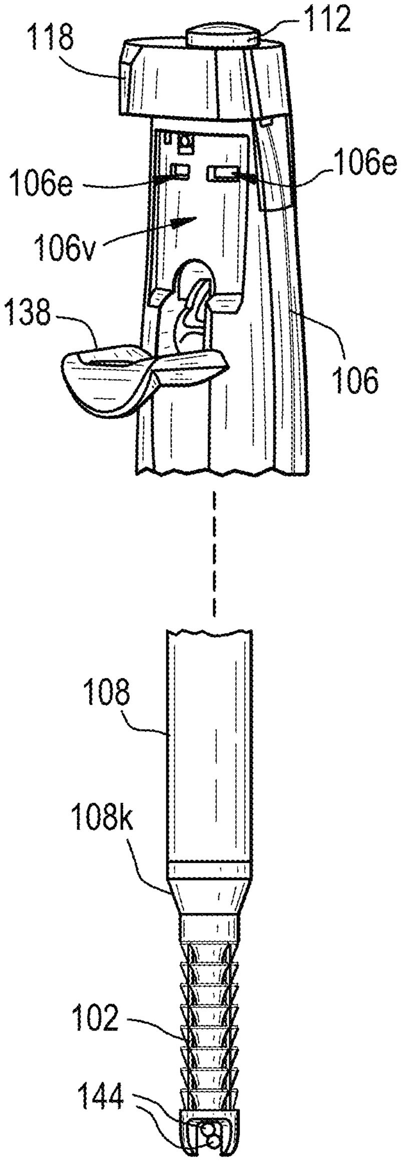
FIG. 31 is a perspective view of proximal and distal portions of the inserter tool of FIG. 30 with the bone omitted and with the retraction mechanism of the inserter tool in an actuated position.
Figure 32:
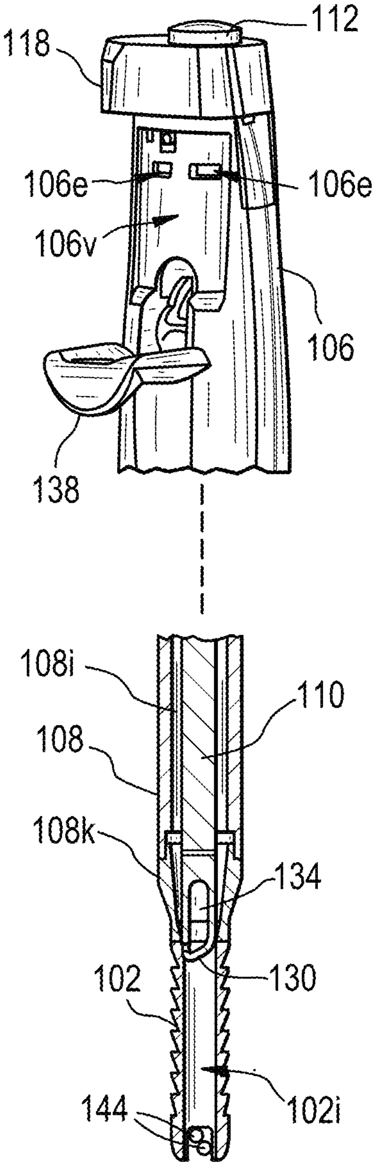
FIG. 32 is a perspective view of proximal and distal portions of the inserter tool of FIG. 31 with the bone omitted and with the inner shaft of the inserter tool retracted with respect to the anchor.
Figure 33:
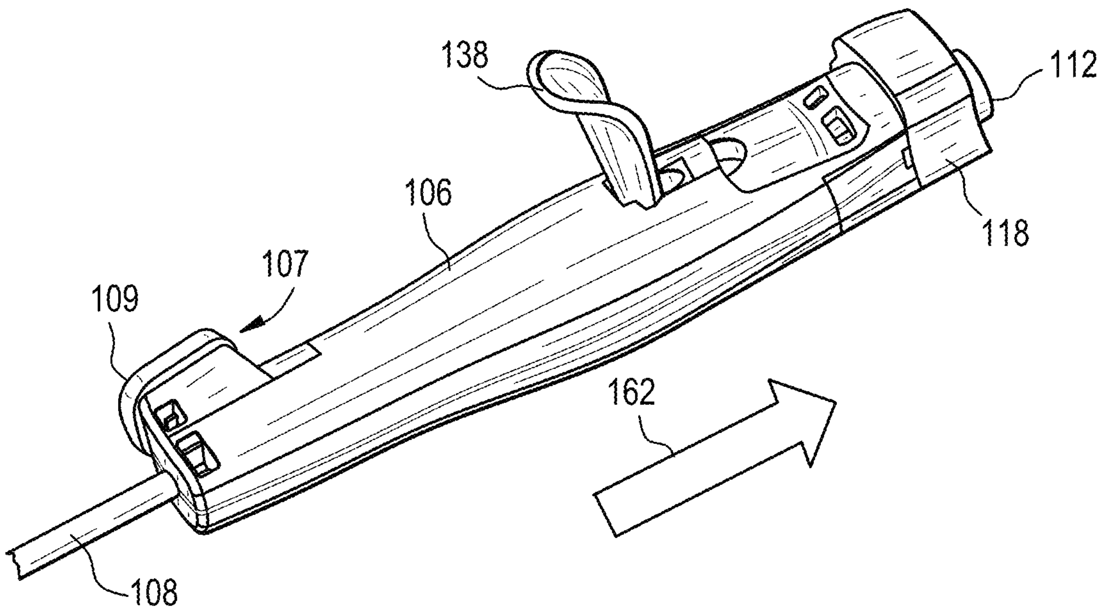
FIG. 33 is a perspective view of a proximal portion of the inserter tool of FIG. 32 showing a direction of removal of the inserter tool.

As shown in FIGS. 1-4, the retraction mechanism 136 is located in a proximal portion of the inserter tool 100 that includes the handle 106. The retraction mechanism 136 is coupled to the handle 106 and is partially housed therein. The proximal portion of the inserter tool 100 including the handle 106 and the retraction mechanism 136 is typically located entirely outside of a patient's body during use of the inserter tool 100. The retraction mechanism 136 is thus easily accessible and visible to a user during use of the inserter tool 100. Conversely, the portion of the inserter tool 100 that is positioned within the anchor 102 after the anchor 102 has been inserted into bone is located in a distal portion of the inserter tool 100 and is located entirely inside the patient's body during use of the inserter tool 100. As discussed further below, the retraction mechanism 136 is configured to move from an initial, unactuated position to an actuated position to remove the inserter tool 100 from within the anchor 102. FIGS. 1-4, 8, and 13-16 show the retraction mechanism 136 in the initial position. FIGS. 31-33, which are discussed further below, show the retraction mechanism 136 in the actuated position. The retraction mechanism 136 being in the actuated position and being visible to a user may therefore visually indicate to the user that the inserter tool 100 has been removed from within the anchor 102 even if the inserter tool 100 and/or the anchor 102 cannot be fully or partially visualized within the patient's body.

The retraction mechanism 136 can have a variety of configurations. In this illustrated embodiment, the retraction mechanism 136 includes a lever. As shown in FIGS. 8 and 13-16, the retraction mechanism 136 includes a lever handle 138, a yoke 140, and a lever lock 142. The lever handle 138 is configured to be moved by a user to actuate the retraction mechanism 136. The lever handle 138 is disposed partially outside of the handle 106 and partially inside the handle 106. The lever handle 138 is thus accessible to and visible by a user from outside of the handle 106 to facilitate actuation and visualization of the retraction mechanism 136. The yoke 140 and the lever lock 142 are disposed inside the handle 106.

Figure 13:
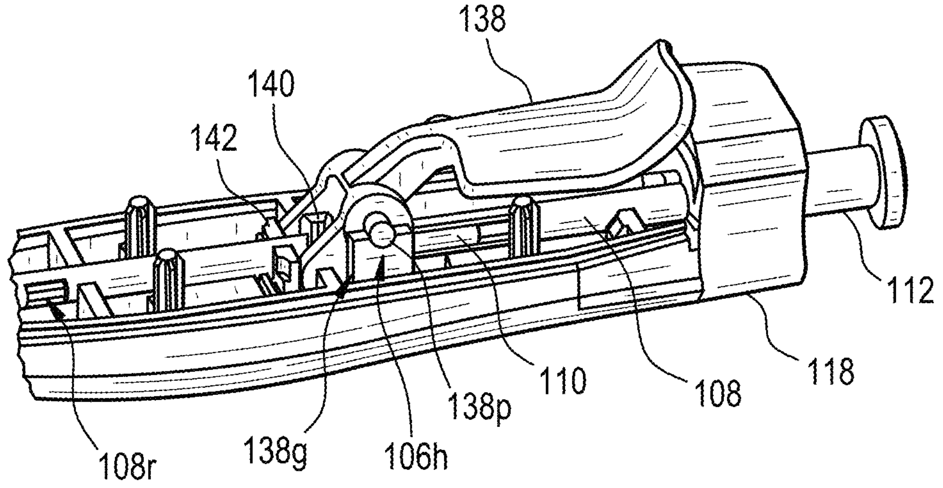
FIG. 13 is a perspective view of a proximal portion of the inserter tool of FIG. 1 with a handle of the inserter tool partially omitted.

As shown in FIG. 13, the lever handle 138 includes a pair of opposed pins 138*p* (one of the pins 138*p* is obscured in FIG. 13) configured to be seated in opposed holes defined by the handle 106. Half 106*h* of one of the holes is shown in FIG. 13 because of the perspective view of FIG. 13 and because the handle 106 is only partially shown in FIG. 13. The pins 138*p* are configured to rotate within their respective holes in response to actuation of the retraction mechanism 136.

Figure 14:
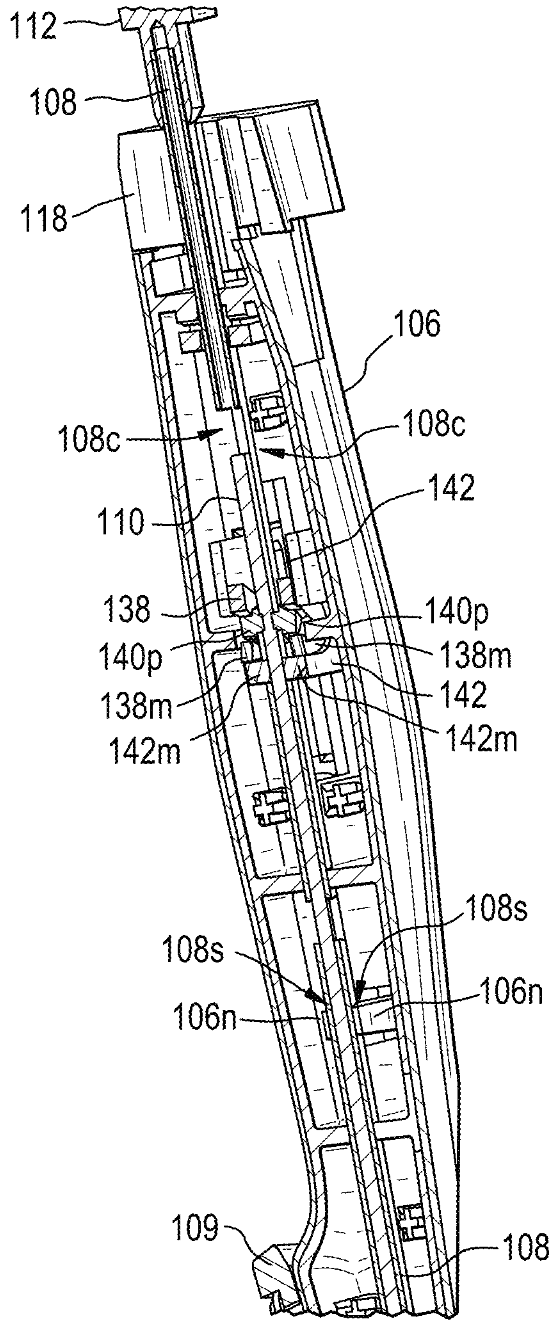
FIG. 14 is a perspective cross-sectional view of a portion of the inserter tool of FIG. 1.
Figure 15:
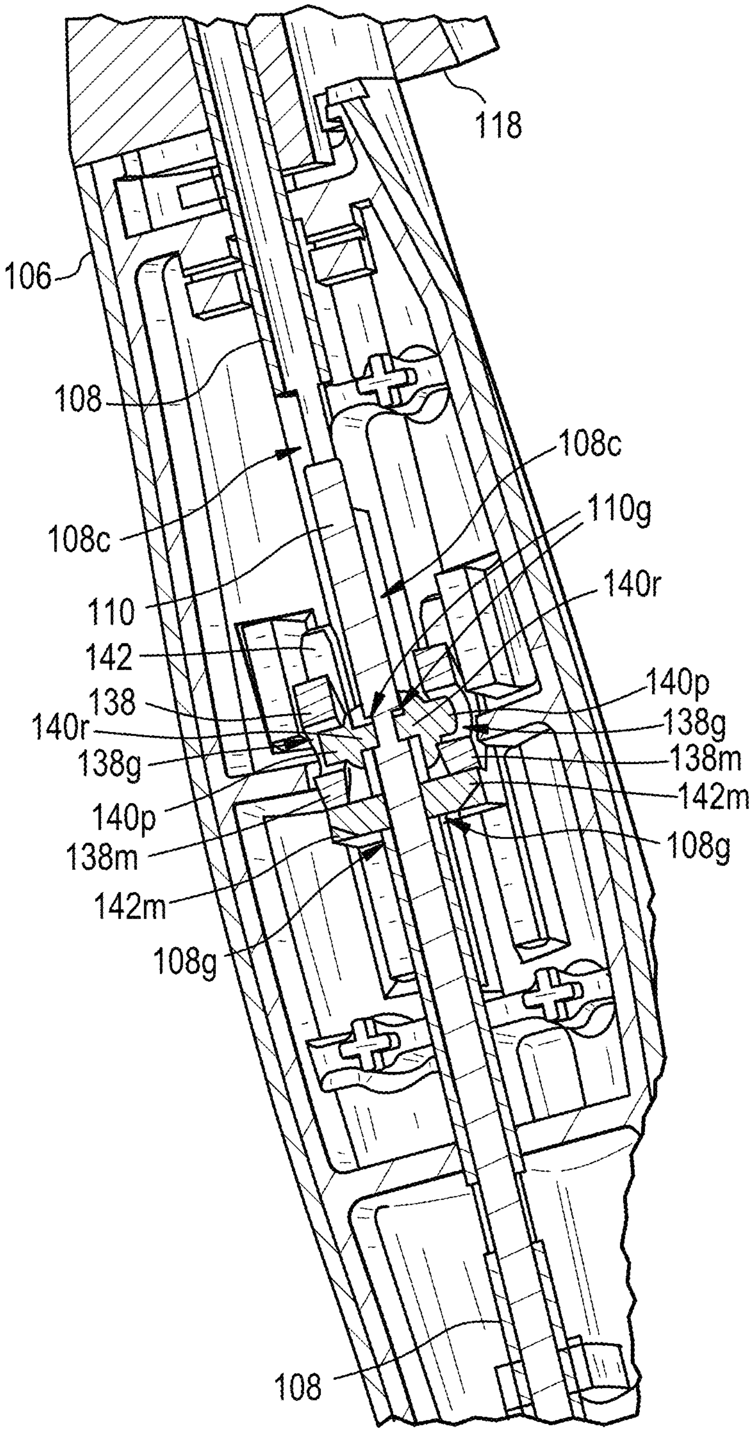
FIG. 15 is another perspective cross-sectional view of a portion of the inserter tool of FIG. 1.

The lever handle 138 also includes a pair of opposed openings 138*g* (see FIGS. 13 and 15) formed in opposed arms 138*m* of the lever handle 138 (see FIGS. 14 and 15). The lever handle's openings 138*g* are each configured to seat therein one of a pair of opposed pins 140*p* of the yoke 140 (see FIGS. 14-16).

The lever handle 138 also includes a pair of mating features (obscured in FIG. 13) on an inner surface thereof that are configured to releasably mate with a pair of mating elements 106*c* of the handle 106 (see FIGS. 31 and 32 showing the mating elements 106*e* in a cavity 106*v* formed in the handle 106). The mating of the mating features and the mating elements 106*e* is configured to help hold the lever handle 138 in position relative to the handle 106 prior to actuation of the retraction mechanism 136. In this illustrated embodiment the mating features are male members and the mating elements 106*e* are female members configured to releasably seat the male members therein, but instead the lever handle 138 can include female mating elements and the handle 106 can include male mating features.

Figure 16:
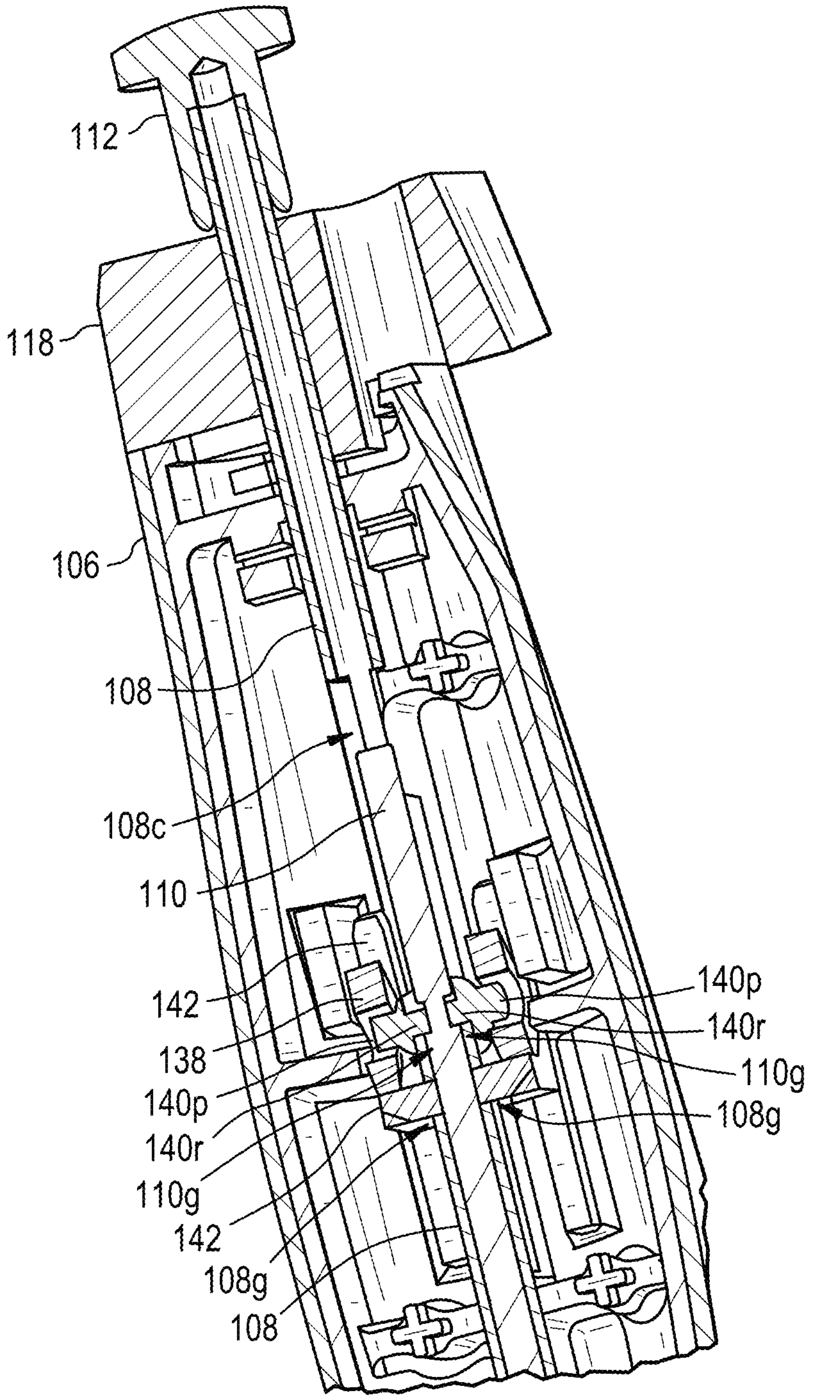
FIG. 16 is another perspective cross-sectional view of a proximal portion of the inserter tool of FIG. 1.

As shown in FIGS. 14-16, the yoke 140 includes a pair of opposed rails 140*r* configured to be seated in opposed longitudinal channels 108*c* formed in the outer shaft 108. As shown in FIGS. 15 and 16, the inner shaft 110 includes a pair of opposed grooves 110*g* formed therein. The yoke's rails 140*r* are each configured to be seated in one of the inner shaft's grooves 110*g*. The inner shaft 110 is disposed within the outer shaft's inner lumen 108*i*, but the rails 140*r* of the yoke 140 are configured to extend through the outer shaft's longitudinal channels 108*c* to be seated in the inner shaft's grooves 110*g*. The rails 140*r* of the yoke 140 are configured to slide proximally within their respective longitudinal channels 108*c* of the outer shaft 108 in response to actuation of the retraction mechanism 136. Because the rails 140*r* of the yoke 140 are seated in the grooves 110*g* of the inner shaft 110, the proximal movement of the yoke 140 is configured to cause corresponding longitudinal movement of the inner shaft 110 (and the suture retainer 132 fixedly attached thereto) in the proximal direction relative to the outer shaft 108, the handle 106, and the anchor 102. The inner shaft 110 (and the suture retainer 132 fixedly attached thereto) can thus be removed from within the anchor 102 by moving proximally out of the anchor 102 in response to actuation of the retraction mechanism 136. The outer shaft 108 is configured as a stop that stops proximal movement of the yoke 140 when the yoke 140, e.g., the rails 140*r* thereof, abuts a proximal end of the outer shaft's longitudinal channels 108*c*.

Figure 26:
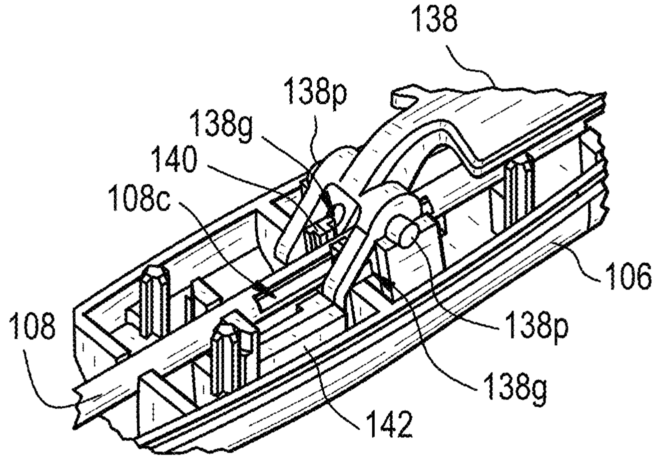
FIG. 26 is a perspective view of a portion of the inserter tool of FIG. 25 with the handle of the inserter tool partially omitted.

As mentioned above, the retraction mechanism 136 is configured to move between the initial, unactuated position and the actuated position. In the unactuated position, the lever lock 142 is in a locked position, in which the lever lock 142 is configured to lock the lever handle 138 and the yoke 140 such that the lever handle 138 cannot be moved by a user to cause retraction of the inner shaft 110 (and the suture retainer 132 fixedly attached thereto). The advancement of the anchor 102 into bone, e.g., by striking the strike cap 112 to push the push tube 108 distally, is configured to cause the lever lock 142 to move from the locked position to an unlocked position, in which the lever lock 142 does not lock the lever handle 138 and the yoke 140 such that the lever handle 138 can be moved by a user to cause retraction of the inner shaft 110 (and the suture retainer 132 fixedly attached thereto). FIGS. 13-16 show the lever lock 142 in the locked position. FIG. 26, which is discussed further below, shows the lever lock 142 in the unlocked position. The retraction mechanism 136 therefore cannot be prematurely actuated before the anchor 102 has been advanced into bone. As discussed further below, the lever lock 142 is fixedly attached to the push tube 108 such that the distal movement of the push tube 108 is configured to cause corresponding longitudinal movement of the lever lock 142 in the distal direction to move the lever lock 142 from the locked position to the unlocked position. The locking mechanism 118, which is configured to lock the push tube 108 as discussed herein, is thus also configured to lock the lever lock 142 and thereby further prevent premature actuation of the retraction mechanism 136 before the anchor 102 has been advanced into bone.

The lever lock 142 is configured to prevent the lever handle 138 from being moved relative to the handle 106 and thus to prevent the yoke 140 and the inner shaft 110 (and the suture retainer 132 fixedly attached thereto) from moving relative to the handle 106. A pair of opposed arms 142*m* of the lever lock 142 are positioned distal to the arms 138*m* of the lever handle 138. The lever lock 142 is thus configured to prevent the lever handle 138 from being moved relative to the handle 106 with the retraction mechanism 136 in the initial, unactuated position because the lever lock 142, e.g., the lever lock's arms 142*m*, prevent the lever handle 138 from being moved relative to the handle 106, e.g., prevent the lever handle's pins 138*p* from rotating within the handle's holes due to the lever handle's arms 138*m* being blocked from movement by the lever lock 142.

As shown in FIGS. 15 and 16, the outer shaft 108 includes a pair of opposed grooves 108*g* formed therein. The lever lock's arms 142*m* are each configured to be seated in one of the outer shaft's grooves 108*g*. Because the arms 142*m* of the lever lock 142 are seated in the grooves 108*g* of the outer shaft 108, the distal movement of the outer shaft 108, e.g., due to striking of the strike cap 112, is configured to cause corresponding longitudinal movement of the lever lock 142 in the distal direction relative to the inner shaft 108, the lever handle 138, the yoke 140, and the handle 106. The lever lock 142 is thus configured to move distally relative to the lever handle 138 such that the arms 138*m* of the lever handle 138 are no longer constrained by the lever lock 142 so as to allow movement of the lever handle 138 relative to the handle 106 to actuate the retraction mechanism 136.

As shown in FIG. 13, the outer shaft 108 also includes a pair of opposed locking slots 108*s* formed therein and a pair of opposed locking grooves 108*r* formed therein proximal to the outer shaft's pair of opposed slots 108*s* and distal to the outer shaft's pair of opposed grooves 108*g*. The handle 106 includes a holding mechanism configured to help hold the outer shaft 108 in its distal position after striking of the strike cap 112. In this illustrated embodiment the holding mechanism includes a pair of opposed fingers 106*n* internal to the handle 106 and each configured to releasably seat in one of the outer shaft's slots 108*s* with the inserter tool 100 in the initial configuration, as shown in FIG. 13. The fingers 106*n* seated in the locking slots 108*s* are configured to help hold the outer shaft 108 in its proximal position prior to the strike cap 112 being struck to distally advance the outer shaft 108 so that the anchor 102 is not prematurely distally advanced by distal movement of the outer shaft 108 relative to the handle 106. The fingers 106*n* are each configured to releasably seat in the one of the outer shaft's locking grooves 108*r* after the outer shaft 108 has been distally advanced to distally advance the anchor 102, e.g., in response to striking of the strike cap 112. The fingers 106*n* seated in the locking grooves 108*r* are configured to help hold the outer shaft 108 in its distal position after striking of the strike cap 112 so that the outer shaft 108 remains in position relative to the handle 106, the anchor 102, and the inner shaft 110 when the retraction mechanism 136 is subsequently actuated to retract the inner shaft 110 (and the suture retainer 132). As the outer shaft 108 moves distally from its position in which the handle's fingers 106*n* are seated in the outer shaft's locking slots 108*s*, the fingers 106*n* are configured to automatically change from being seated in the locking slots 108*s* to being seated in the locking grooves 106*r*. Each of the fingers 106*n* has a free end, which allows the fingers 106*n* to flex if needed as the outer shaft 108 moves distally relative to the handle 106 to move the fingers 106*n* out of the locking slots 108*s* and into the locking grooves 108*g*. The fingers 106*n* slide proximally along the outer shaft 108 until becoming seated in the locking grooves 106*g*.

FIGS. 19-35 illustrate one embodiment of a method of using an inserter tool. Although the method is described with respect to the inserter tool 100, the anchor 102, and the loading aid 122 of FIGS. 1-5, other inserter tools, anchors, and loading aids can be similarly used. Also, as mentioned above, a loading aid need not be used at all.

FIGS. 17-20 show various portions of the inserter tool 100 at a same time in the method in which a suture 144 is loaded onto the inserter tool 100 using the loading aid 122. The inserter tool 100 is in the initial configuration (see FIGS. 17-20), the loading aid 122 is coupled to the inserter tool 100 (see FIG. 17), the locking mechanism 118 is in its locked position (see FIGS. 18 and 19), the retraction mechanism 136 is in the unactuated position (see FIGS. 18 and 19), the lever lock 142 is in its locked position, and the handle's fingers 106*n* are seated in the outer shaft's locking slots 108*s* (see FIG. 20).

The suture 144 includes a single strand in this illustrated embodiment but can include a plurality of strands. The suture 144 is coupled to, e.g., tied to, threaded through, etc., a tissue 146 to be positioned relative to bone. The tissue 146 can be any of a variety of tissues, natural or artificial, as appropriate for the particular surgical procedure being performed, such as a labrum for a rotator cuff repair procedure.

Figure 17:
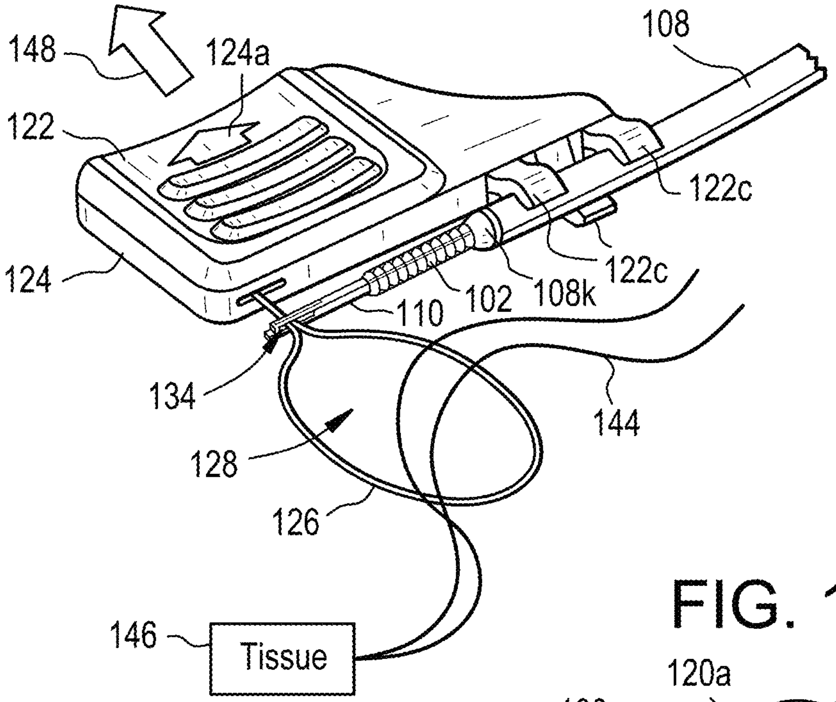
FIG. 17 is a perspective view of the loading aid and a distal portion of the inserter tool of FIG. 3 with one embodiment of a suture extending through a loop of the loading aid.
Figure 19:
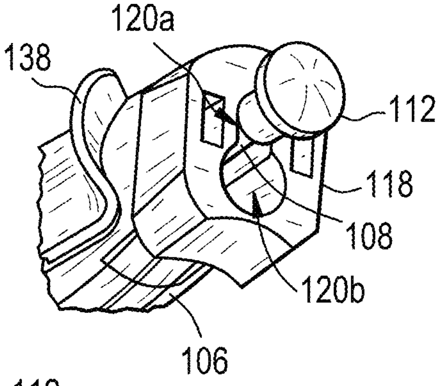
FIG. 19 is another perspective view of a proximal portion of the inserter tool of FIG. 17.
Figure 18:
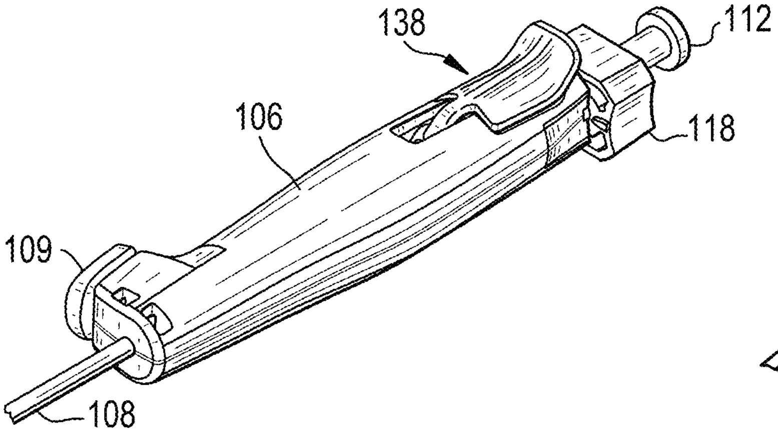
FIG. 18 is a perspective view of a proximal portion of the inserter tool of FIG. 17.
Figure 20:
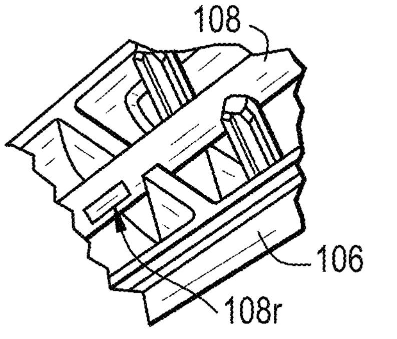
FIG. 20 is another perspective view of a portion of the inserter tool of FIG. 17 with the handle of the inserter tool partially omitted.

As shown in FIG. 17, the loading aid 122 is releasably coupled to the inserter tool 100, and the suture 144 extends through the loop 126 of the loading aid 122. With the suture 144 extending through the loop 126 of the loading aid 122, the loading aid 122 is pulled by the base 124 to pull the suture 144 through the inserter tool's enclosed passage 134 such that the suture 144 extends through the enclosed passage 134. The loading aid 122 is pulled in a direction shown by an arrow 148 in FIG. 17, which corresponds to the direction of the arrow 124*a* on the base 124, to pull the suture 144 through the enclosed passage 134.

Figure 21:
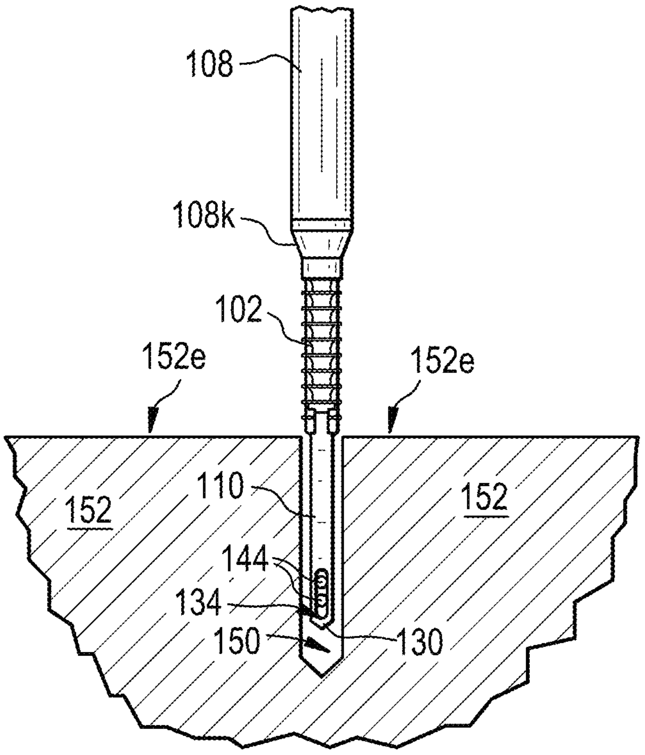
FIG. 21 is a side, partially cross-sectional view of a distal portion of the inserter tool of FIG. 17 with the suture coupled thereto and with a distal portion of the inner shaft of the inserter tool disposed in one embodiment of a bone hole.

With the suture 144 coupled to the inserter tool 100 by being seated in the enclosed passage 134, and thus also seated in the suture retention channel 116, and with the loading aid 122 removed from the inserter tool 100 (if the loading aid 122 was used to facilitate suture coupling to the inserter tool 100), the inserter tool 100 is used to insert the suture 144 and the anchor 102 into a bone hole 150 formed in bone 152 (see FIG. 21). In an exemplary embodiment of using the inserter 100 to insert the suture 144 and the anchor 102 into the bone hole 150, a drill or other bone removal tool is inserted into a patient's body to form the bone hole 150, as will be appreciated by a person skilled in the art. The drill or other bone removal tool can be advanced into the patient's body, and then removed from the patient's body, through a cannula positioned within an opening, e.g., an incision, formed in the patient's skin, as will also be appreciated by a person skilled in the art. The cannula can then serve as a guide for the inserter's distal advancement toward the bone hole 150.

Figure 22:
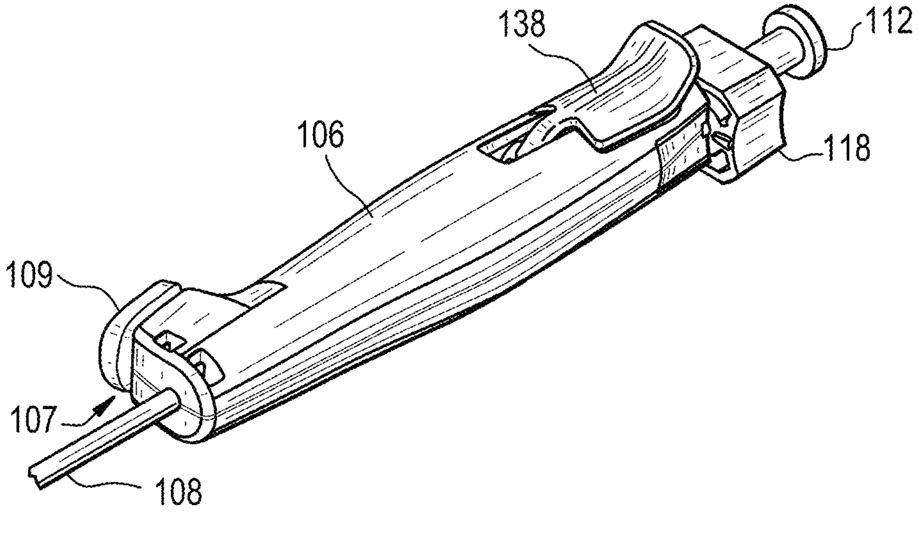
FIG. 22 is a perspective view of a proximal portion of the inserter tool of FIG. 21.

The inserter 100 is advanced distally into the body of the patient and positioned with the distal end of the inner shaft 110 within the bone hole 150, as shown in FIG. 21. FIGS. 21 and 22 show distal and proximal portions of the inserter tool 100, respectively, at a same time in the method. The suture 144 that extends through the enclosed passage 134 and the suture retention channel 116 is thus positioned in the bone hole 150 before the anchor 102 is secured in the bone hole 150. A bottom surface of the bone hole 150 can act as a stop surface that stops distal movement of the inserter 100 relative to the bone 152, e.g., by abutting the inner shaft 110 and/or the suture retainer 132, and/or an external surface 152*e* of the bone 152 can serve as a stop surface that stops distal movement of the inserter 100 relative to the bone 152, e.g., by abutting the anchor 102 or the bushing 108*k*. An interior of the bone hole 150 cannot be visualized with the inserter 100 positioned in the bone hole 150, so a stop can help ensure that the inserter 100 has been advanced as far as distally possible within the bone hole 150, which may help ensure that the anchor 102 is secured in the bone hole 150 with the anchor's proximal end flush or sub-flush with a proximal end of the bone hole 150. Alternatively, the inserter 100 can be inserted into the bone hole 150 only a specified distance prior to a distal end of the anchor 102 engaging an open proximal end of the bone hole 150. As the anchor 102 is not readily advanced into the bone hole 150 without impacting the strike cap 112, the distance the inserter 100 protrudes from the anchor 102 controls the distance that the inserter 100 will advance into the bone hole 150.

Figure 23:
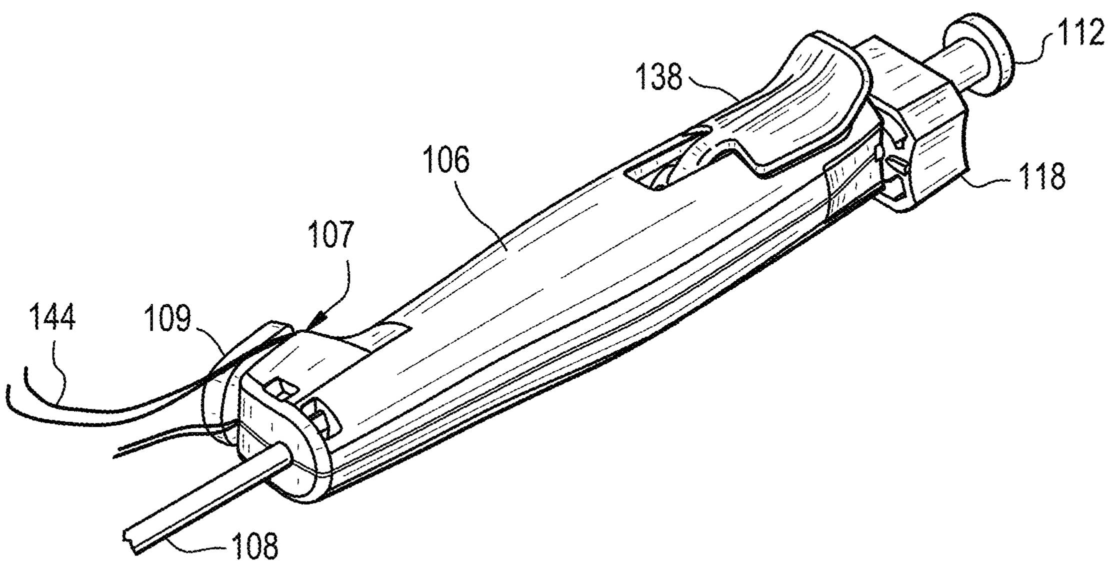
FIG. 23 is a perspective view of the proximal portion of the inserter tool of FIG. 22 with the suture retained by a suture retention member of the inserter tool.

With the distal end of the inner shaft 110 positioned in the bone hole 150, and prior to distal advancement of the anchor 102 relative to the inner shaft 110, the suture 144 can be tensioned as desired. Alternatively, the suture 144 tension can be approximated prior to placement of the inserter 100 into the bone hole 150, with the advancement of the inserter 100 into the bone hole 150 adding tension approximately equal to a length of the inserter's distance protruding from the distal end of the anchor 102. A person skilled in the art will appreciate that values may not be precisely equal but nevertheless considered to be approximately equal for any of one or more reasons, such as manufacturing tolerances or sensitivity of measurement equipment. With the suture 144 desirably tensioned, the suture 144 is seated in the groove 107, as shown in FIG. 23, so as to be retained by the suture retention member with the suture's tension maintained.

Figure 24:
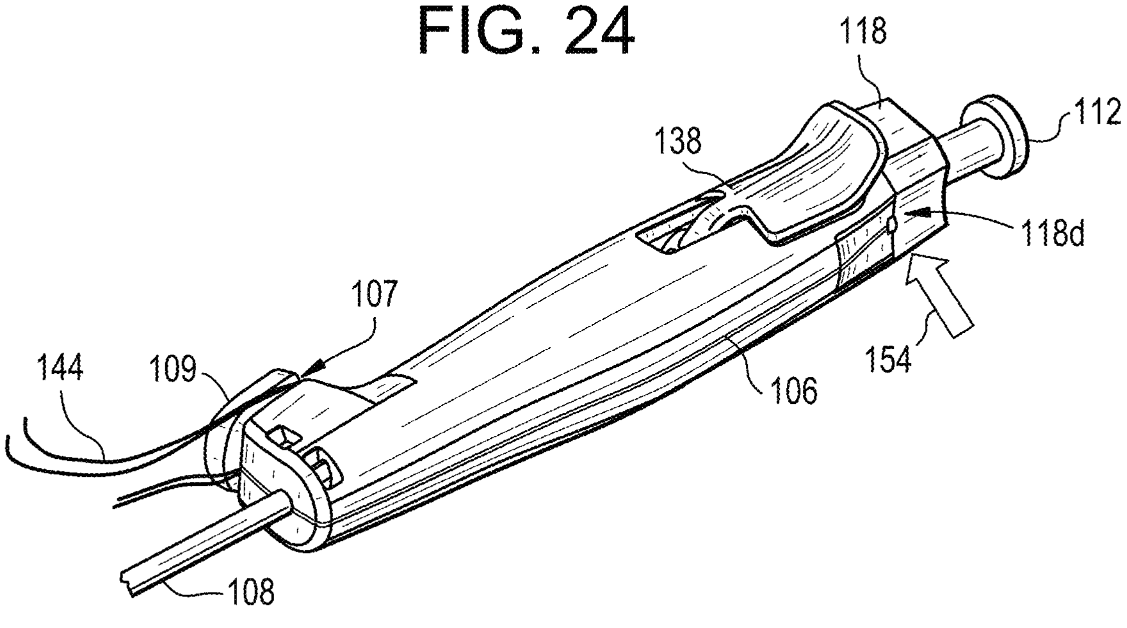
FIG. 24 is a perspective view of the proximal portion of the inserter tool of FIG. 23 with the locking mechanism of the inserter tool in the unlocked position.

With the suture 144 and the distal end of the inner shaft 110 positioned in the bone hole 150, the locking mechanism 118 is moved from the locked position to the unlocked position. FIG. 24 shows the locking mechanism 118 in the unlocked position, having moved from the locked position of FIGS. 18, 19, 22, and 23 by being pushed as shown by an arrow 154 to move relative to the handle 106, the outer shaft 108, and the strike cap 112. The outer shaft 108 is now free to move relative to the inner shaft 110 in response to a strike on the strike cap 112. The locking mechanism 118 can be moved from the locked position to the unlocked position after the suture 144 has been tensioned and retained by the suture retention mechanism in this illustrated embodiment, but the locking mechanism 118 can be moved from the locked position to the unlocked position before the suture 144 has been tensioned and retained by the suture retention mechanism.

Figure 25:
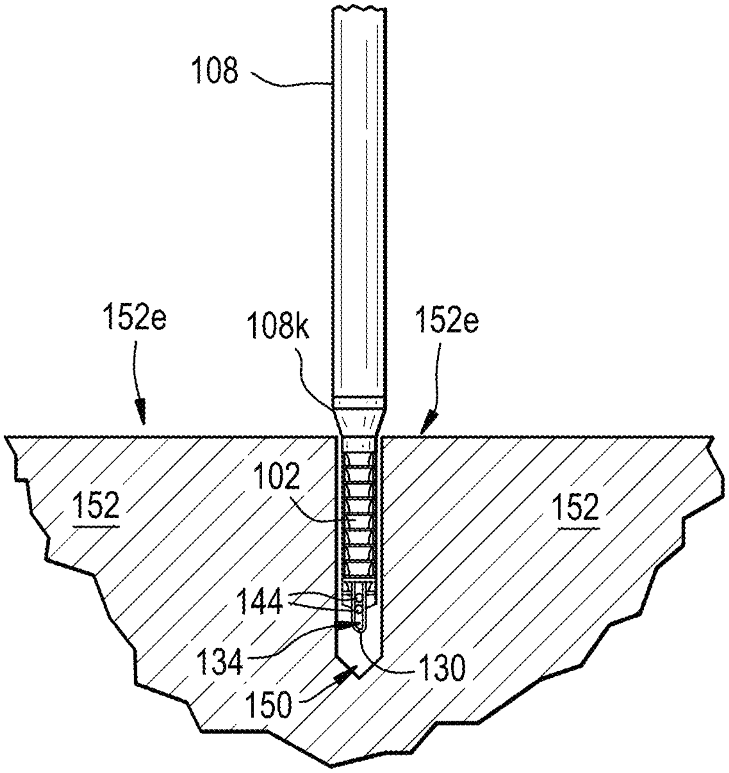
FIG. 25 is a side, partially cross-sectional view of the distal portion of the inserter tool of FIG. 24 with the anchor disposed in the bone hole.

With the distal end of the inner shaft 110 positioned in the bone hole 150 and the locking mechanism 118 in the unlocked position, the anchor 102 is advanced distally into the bone hole 150 by longitudinally translating the anchor 102 relative to the inner shaft 110 in a distal direction. In other words, the anchor 102 is pushed axially along the longitudinal axis of the inserter 100. The strike cap 112 is hit with a mallet, hammer, or other tool to cause the outer tube 108 to move distally relative to the inner shaft 110, which causes the anchor 102 to move distally relative to the inner shaft 110 and advance distally into the bone hole 150, as shown in FIG. 25. The anchor 102 is positioned sub-cortically, e.g., by about 1 mm or by another amount, in the illustrated embodiment of FIG. 25 so as to be positioned sub-flush in the bone 152. The strike cap 112 may be hit one or more times to fully advance the anchor 102 into the bone hole 150. The bushing 108*k* can include an indicator, e.g., a laser line thereon, a groove formed therein, etc., configured to align with the external surface 152*e* of the bone 152 to visually indicate to a user that the anchor 102 has been fully distally advanced into the bone hole 150, as the anchor 102 being positioned sub-flush in the bone 152 prevents visualization of the anchor 102 in the bone hole 150 (at least before the inserter 100 is removed from the anchor 102). The anchor 102 in the bone hole 150 traps the suture 144, e.g., the legs thereof, between an exterior surface of the anchor 102 and a bone surface defining the bone hole 150.

Figure 27:
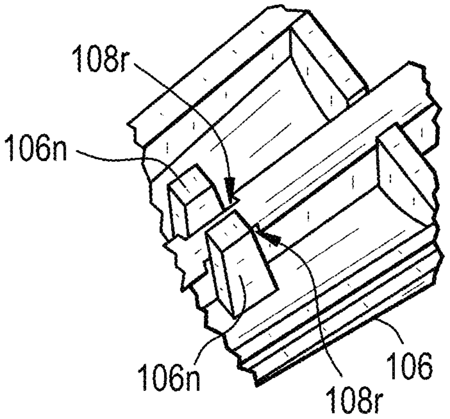
FIG. 27 is another perspective view of a portion of the inserter tool of FIG. 26 with the handle of the inserter tool partially omitted.
Figure 28:
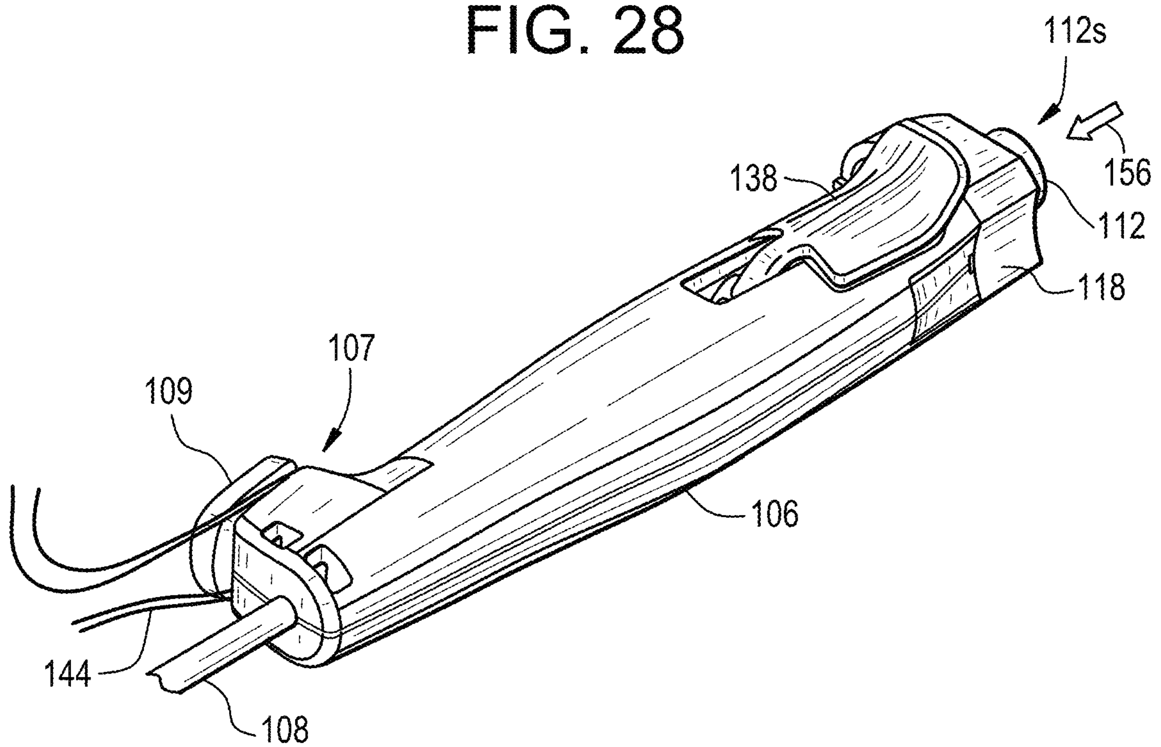
FIG. 28 is a perspective view of the proximal portion of the inserter tool of FIG. 27 after striking of the strike cap.

FIGS. 25-28 show various portions of the inserter tool 100 at a same time in the method. FIG. 25 shows the anchor 102 fully advanced distally in the bone hole 150 as caused by the distal, axial translation of the outer shaft 108. The outer shaft 108, e.g., the bushing 108*k* thereof, abuts the proximal end 102*p* of the anchor 102. FIG. 26 shows that the distal advancement of the outer shaft 108 has caused the lever lock 142 to advance distally and thereby move from its locked position to its unlocked position. FIG. 27 shows that the distal advancement of the outer shaft 108 has caused the handle's fingers 106*n* to be seated in the outer shaft's locking grooves 108*r* after having been seated in the outer shaft's locking slots 108*s* and sliding along the outer shaft 108 as the outer shaft 108 moves distally relative to the fingers 106*n*. FIG. 28 shows the strike cap's distal surface abutting the locking mechanism 118 after the striking of the strike cap 112 in a distal direction shown by an arrow 156.

Figure 29:
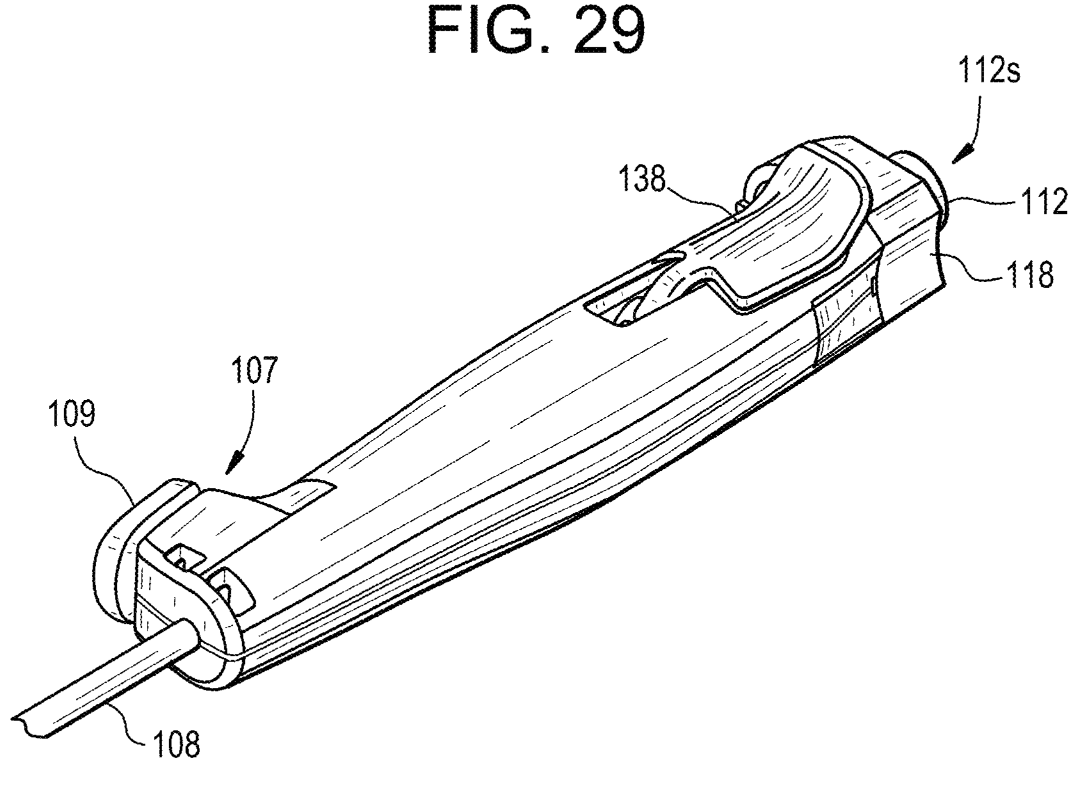
FIG. 29 is a perspective view of the proximal portion of the inserter tool of FIG. 28 without the suture retained by the suture retention member of the inserter tool.

As shown in FIG. 28, the suture 144 is still retained by the suture retention member. The suture 144 is also fixed in the bone hole 150 by the anchor 102 having been advanced into the bone hole 150 and can thus be released from the suture retention member, as shown in FIG. 29 in which the suture 144 is no longer seated in the groove 107.

Figure 30:
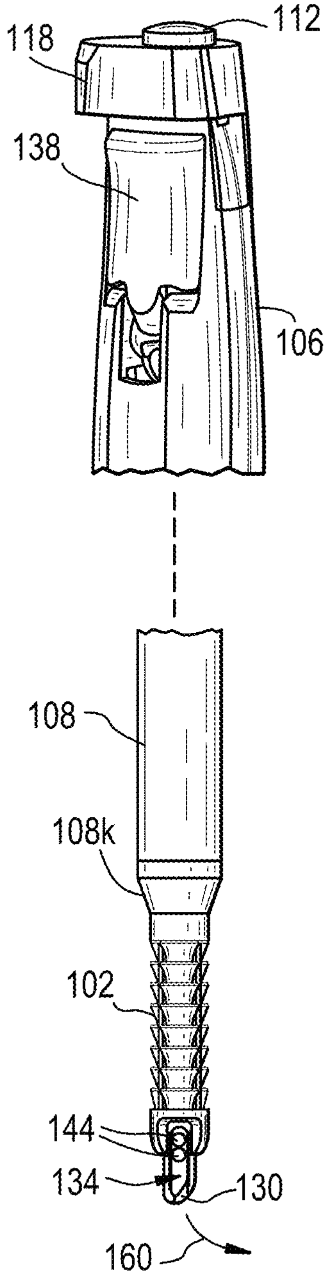
FIG. 30 is a perspective view of proximal and distal portions of the inserter tool of FIG. 29 with the bone omitted and with a retraction mechanism of the inserter tool in an unactuated position.

As shown in FIG. 25, corresponding to a same inserter tool 100 state as FIG. 28, a distal portion of the inserter tool 100 including the inner shaft 110 and the suture retainer 132 is positioned in the bone hole 150 and in the inner lumen 102*i* of the anchor 102 with the anchor 102 and the suture 144 fixed in the bone hole 150. The retraction mechanism 136 is actuated to retract the inner shaft 110 (and the suture retainer 132 fixedly attached thereto) proximally relative to the outer shaft 108, the handle 106, and the anchor 102 to remove the inserter tool 100 from within the anchor 102. To actuate the retraction mechanism 136, the lever handle 138 is moved relative to the inserter handle 106, as shown in FIGS. 30 and 31. FIG. 30 shows the lever handle 138 in the unactuated position, and FIG. 31 shows the lever handle 138 in the actuated position. The lever handle 138 in this illustrated embodiment is configured to pivot about 90° from the unactuated position to the actuated position. A person skilled in the art will appreciate that values, such as angular values, may not be precisely at a value but nevertheless considered to be about the value for any of one or more reasons, such as manufacturing tolerances or sensitivity of measurement equipment. The lever handle 138 pivoting about 90° may provide a clear visual indication to a user that the retraction mechanism 136 has been actuated because the lever handle 138 in the actuated position will protrude substantially perpendicular to the inserter handle 106. The lever handle 138 in this illustrated embodiment is curved at a proximal end thereof, which indicates a direction in which the lever handle 138 should be pivoted to actuated the retraction mechanism.

FIG. 31 shows that the lever handle 138 in the actuated position is no longer seated in the handle's cavity 106*v* and that the lever handle's mating features are no longer mated with the handle's mating elements 106*e* that are located in the cavity 106*v*. The lever handle 138 being seated in the cavity 106*v* may help reduce a profile of the proximal portion of the inserter tool 100 and/or help keep the lever handle 138 out of the way prior to actuation of the retraction mechanism 136.

The lever handle's pins 138*p* rotate in the handle's holes during the actuation of the lever handle 138 as the lever handle 138 moves from its unactuated position (FIG. 30) to its actuated position (FIG. 31) with the handle 106 serving as a fulcrum for the lever handle's pivoting. The lever handle 138 is in a fixed axial position relative to the handle 106 due to the pins 138*p* being seated in the handle's holes, so the lever handle 138 does not translate longitudinally when actuated. The retraction mechanism's yoke 140 is not in a fixed position relative to the handle 106, so the yoke 140 that is operably coupled to the lever handle 138 is free to translate longitudinally relative to the handle 106 in response to the pivoting of the lever handle 138. The yoke 140 slides proximally within the outer shaft's longitudinal channels 108*c*, as discussed above, as the lever handle 138 moves from its unactuated position to its actuated position. The inner shaft 110 (and the suture retainer 132 fixedly attached thereto) thus correspondingly translate proximally relative to the outer shaft 108, the handle 106, and the anchor

102 to pull the inner shaft 110 (and the suture retainer 132 fixedly attached thereto) out of the anchor 102.

The actuation of the retraction mechanism 136 causes the pliable member 130 to bend. The pliable member 130 in this illustrated embodiment is passive by being configured to automatically bend in response to a force applied thereto. As the inner shaft 110 and the suture retainer 132 move longitudinally in the proximal direction relative to the anchor 102 as the retraction mechanism 136 is actuated, the pliable member 130 will encounter the suture 144 in the enclosed passage 134 and the suture retention channel 116. As shown in FIG. 30, the pliable member 130 flexes in a direction of an arrow 160 in response to a force applied thereto by the suture 144 as the pliable member 130 is being pulled proximally with the inner shaft 110. The enclosed passage 134 thus ceases to exist, as discussed above, with the pliable member 130 no longer providing a distal end of the enclosed passage 134. The suture 144 can therefore exit the suture retention channel 116 out of the suture retention channel's open distal end and remain in the bone hole 150, as shown in FIGS. 31 and 32, after the inner shaft 110 and the suture retainer 132 have been removed from the anchor 102. FIG. 32 also shows that the pliable member 130 bends back to its resting configuration after passing proximally past the suture 144 because the suture 144 no longer applies a force to the pliable member 130 to urge the flexing of the pliable member 130.

Figure 34:
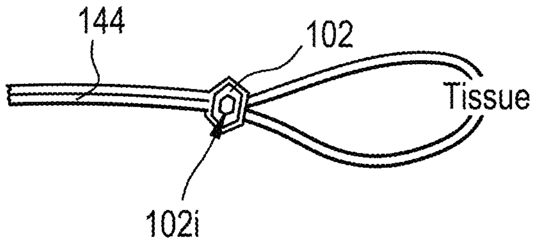
FIG. 34 is a top view of the bone hole, the anchor, and the suture of FIG. 32 after the removal of the inserter tool.
Figure 35:
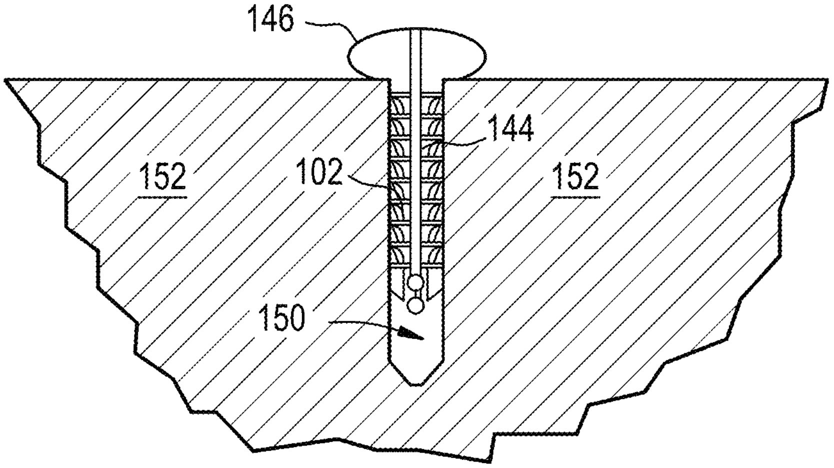
FIG. 35 is a side cross-sectional view of the bone hole, the anchor, and the suture of FIG. 34.

After the retraction mechanism 136 has been actuated, the inserter tool 100 is longitudinally translated in a proximal direction, e.g., pulled axially along a longitudinal axis of the inserter tool 100, as shown by an arrow 162 in FIG. 33, to be removed from the patient's body with the anchor 102 and the suture 144 remaining in the bone hole 150 with the legs of the suture 144 extending out of the bone hole 150. FIGS. 34 and 35 show the anchor 102 and the suture 144 fixed in the bone hole 150 with the tissue 146 coupled to the suture 144 secured in position relative to the bone 152.

The outer and inner shafts 108, 110 of the inserter tool 100 of FIGS. 1-5 are linear. In other embodiments, an inserter tool can have curved outer and inner shafts. Outer and inner shafts of an inserter tool being curved in at least a distal portion thereof may facilitate approach of the inserter tool's distal end to a target site for implantation of an anchor releasably coupled to the inserter tool since the tight constraints of patient anatomy at joints can make it difficult to approach a target site.

FIGS. 36-39 illustrate one embodiment of an inserter tool 200 having curved outer and inner shafts 208, 210. The inserter tool 200 is for knotless anchor insertion in a soft tissue repair surgical procedure and is the same as the inserter tool 100 of FIGS. 1-5 except for the curvature of the outer and inner shafts 208, 210, e.g., is configured to insert the anchor 102 into a bone of a patient to secure a soft tissue relative to the bone and includes a handle 206, the outer shaft 208 that extends distally from the handle 206 and that includes a bushing **208*k*, the inner shaft 210 that extends distally from the handle 206 and that includes a notch formed therein that defines a suture retention channel, a suture retainer including a pliable member 230 (see FIG. 40) that cooperates with the inner shaft 210 to define an enclosed passage 234, a suture retention member in the form of a groove 207 defined by the handle 206 and an elastomeric cleat 209 fixedly attached to the handle 206, a strike cap 212 that extends proximally from the handle 206, a locking mechanism 218 configured to lock the outer shaft 208 in position relative to the inner shaft 210 when the locking mechanism 218 is in a locked position, and a retraction mechanism 236 configured to cause the inserter tool 200 to be removed from within the anchor 102. The retraction mechanism 236 is the same as the retraction mechanism 136 discussed above, e.g., is configured as a lever and includes a lever handle 238, a yoke (obscured in FIGS. 36-39), and a lever lock (obscured in FIGS. 36-39). The inserter tool 200 is shown in FIGS. 36-39 coupled to the anchor 102 of FIGS. 1-7 but can be similarly used with another anchor, similar to that discussed above regarding the anchor 102 and the inserter tool 100. FIGS. 36-40 illustrate the inserter 200** in the initial configuration.

The inserter tool 200 includes an indicator configured to indicate the direction of the outer and inner shafts' curvature to a user, e.g., in the event that the outer and inner shafts' curvature is not visible within the patient's body. In this illustrated embodiment the elastomeric cleat 209 and the handle 206 cooperate as the indicator. The handle 206 has a curvature out toward the elastomeric cleat 209. The curvature of the handle 206 is curved in a same direction as the outer and inner shafts 208, 210. Other embodiments of indicators are described, for example, in previously mentioned U.S. Pat. Pub. No. 2021/0338223 entitled "Knotless Anchor Insertion" published Nov. 4, 2021.

Figure 3:
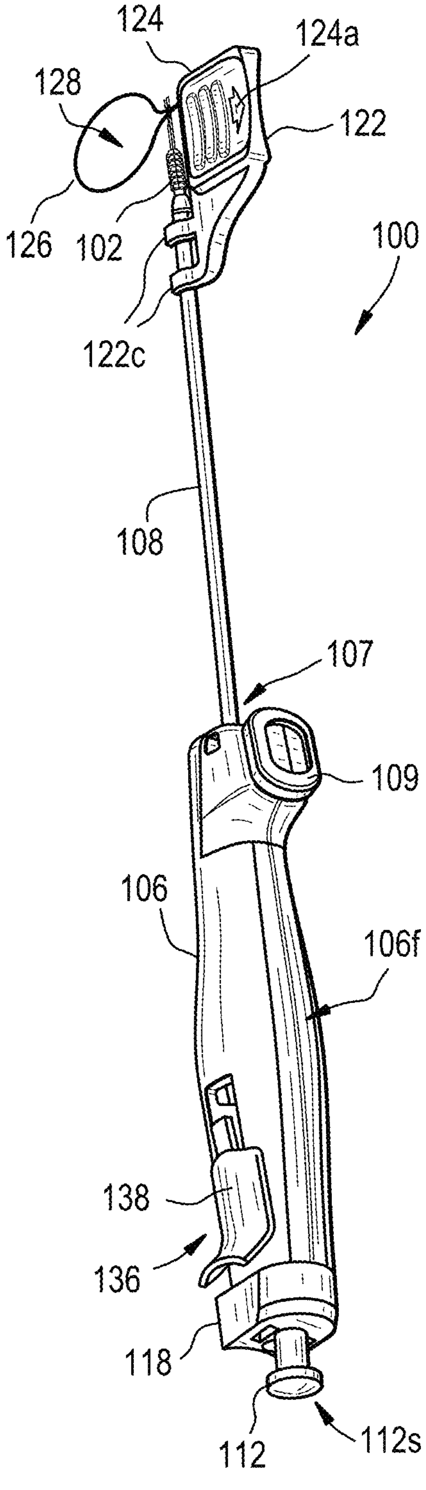
FIG. 3 is another perspective view of the inserter tool and the anchor of FIG. 1 and one embodiment of a loading aid coupled to the inserter tool.
Figure 4:
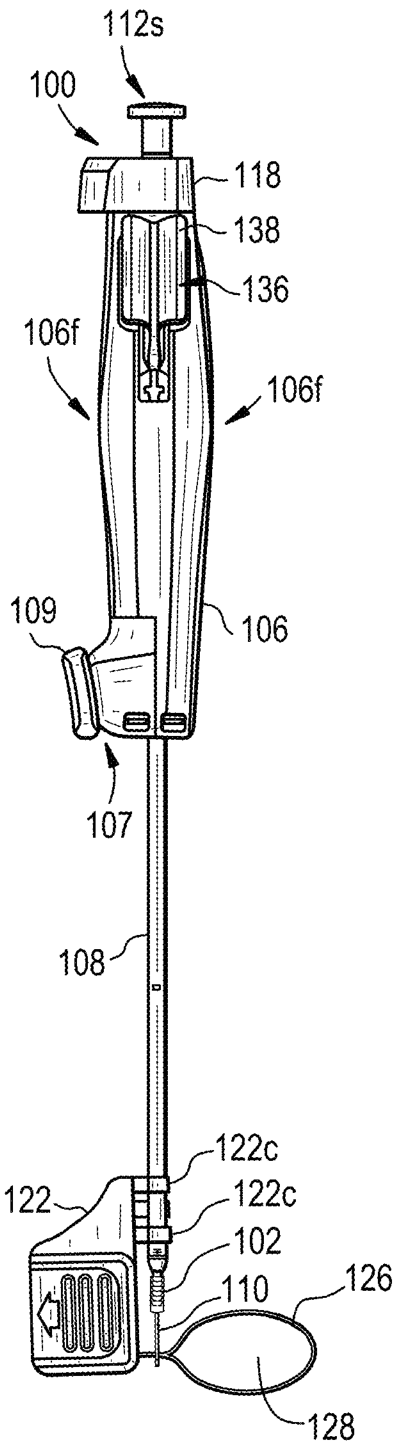
FIG. 4 is a top view of the inserter tool, the anchor, and the loading aid of FIG. 3.
Figure 5:
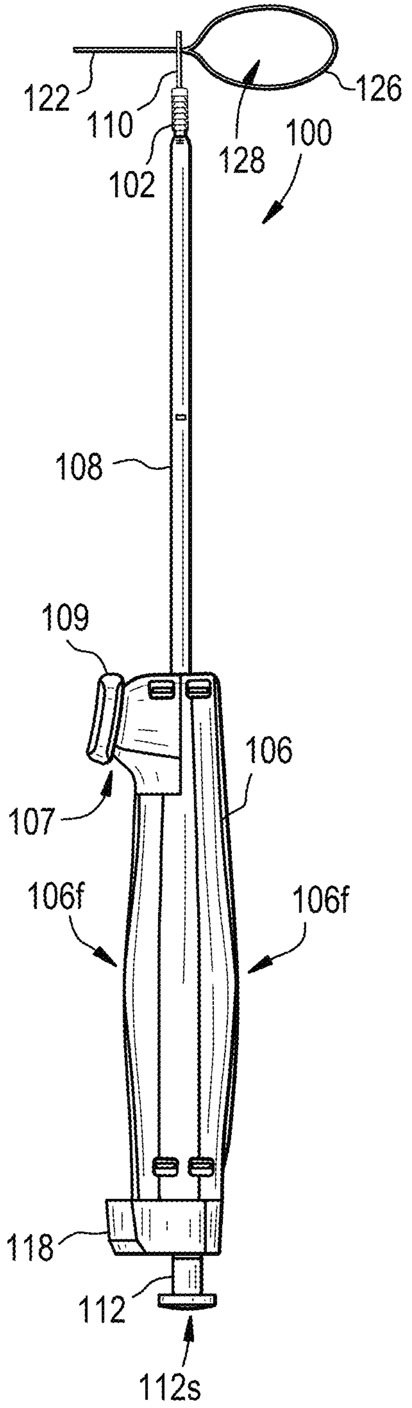
FIG. 5 is a side view of the inserter tool, the anchor, and the loading aid of FIG. 3.
Figure 36:
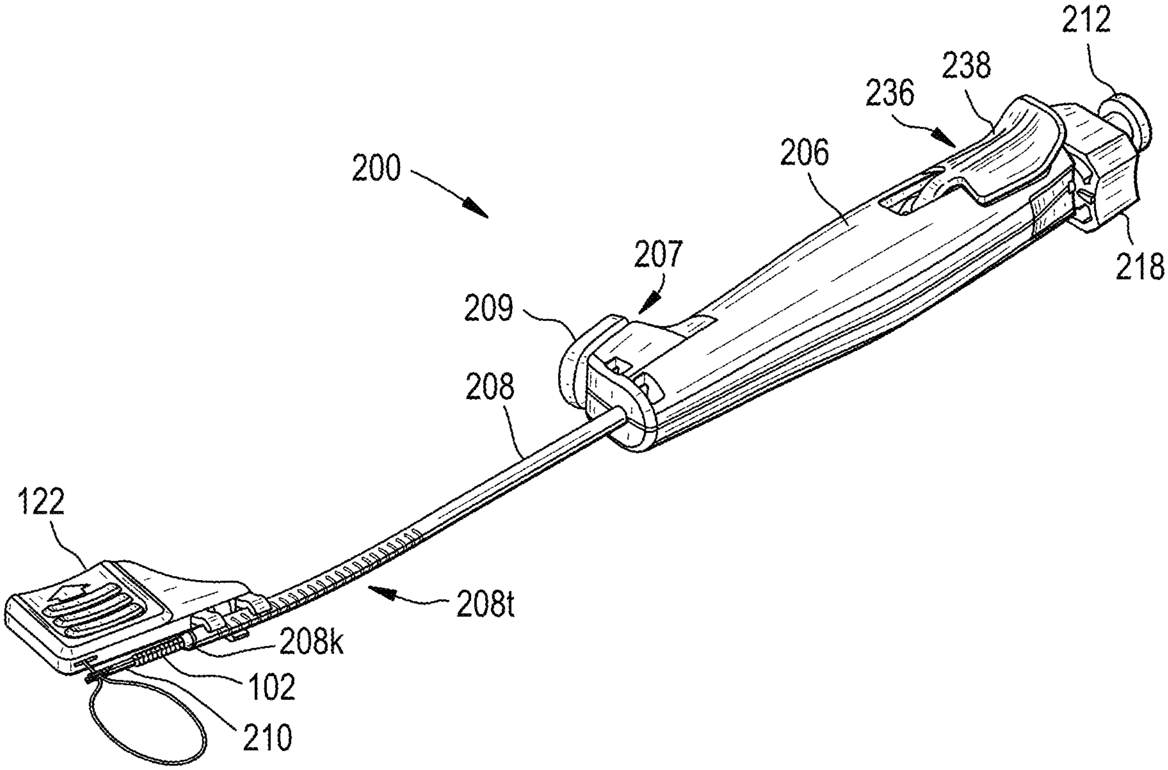
FIG. 36 is a perspective view of another embodiment of an inserter tool coupled to the anchor of FIG. 1 and the loading aid of FIG. 3.
Figure 37:
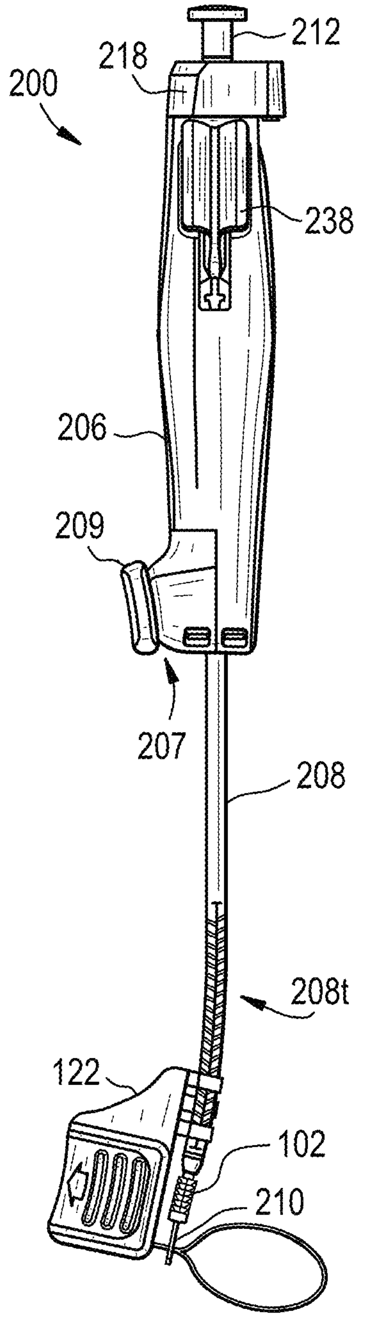
FIG. 37 is a top view of the inserter tool, the anchor, and the loading aid of FIG. 36.
Figure 38:
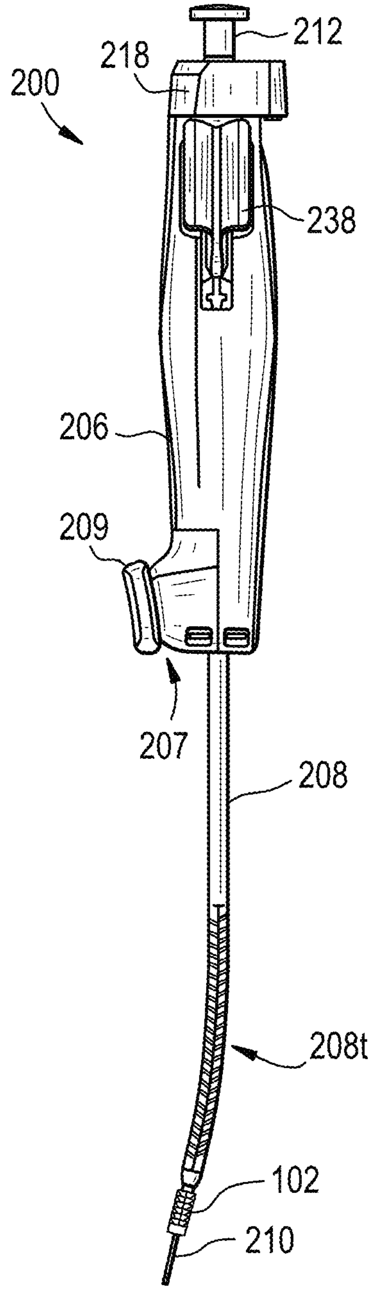
FIG. 38 is a top view of the inserter tool and the anchor of FIG. 37.
Figure 39:
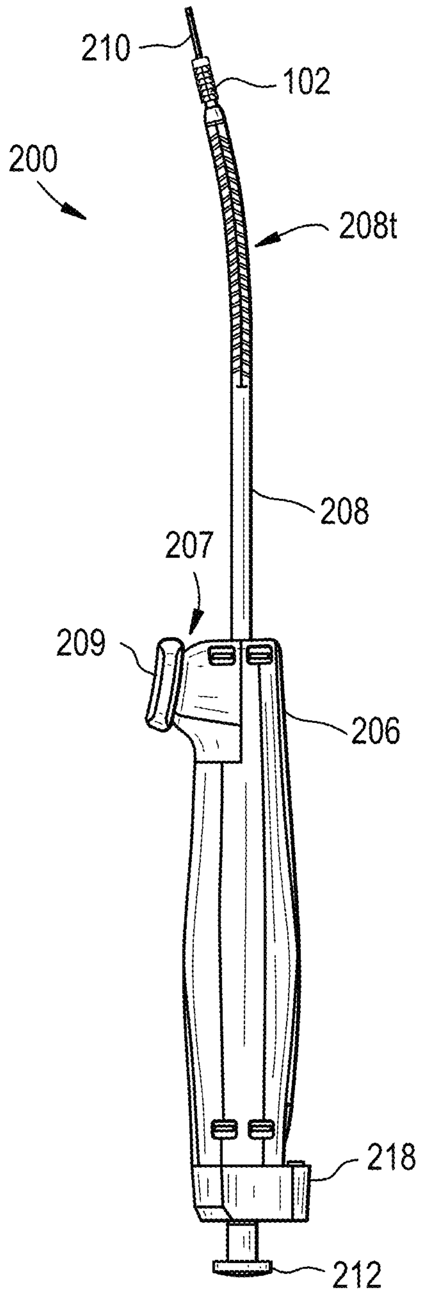
FIG. 39 is a side view of the inserter tool and the anchor of FIG. 37.
Figure 40:
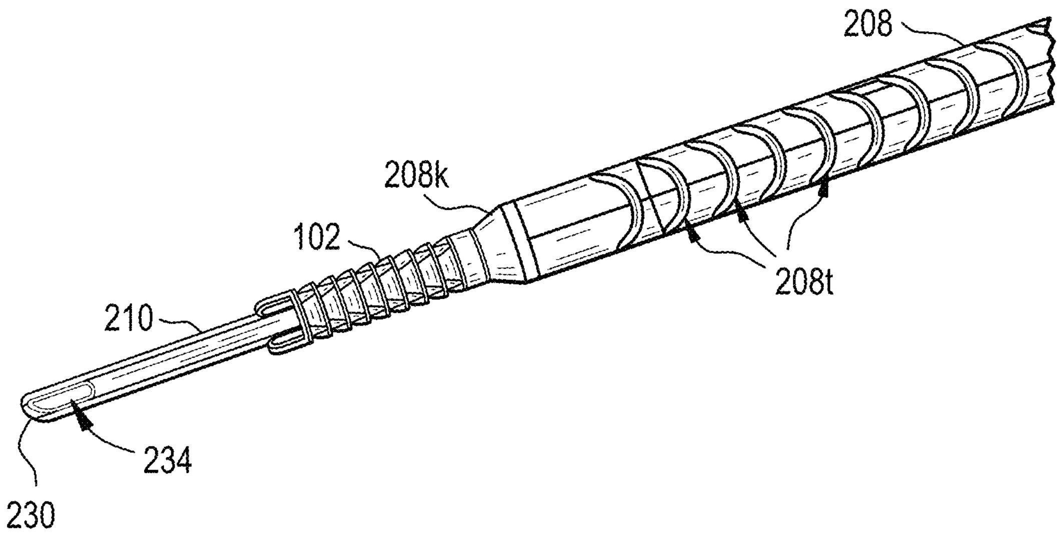
FIG. 40 is a perspective view of a distal portion of the inserter tool and the anchor of FIG. 38.
Figure 41:
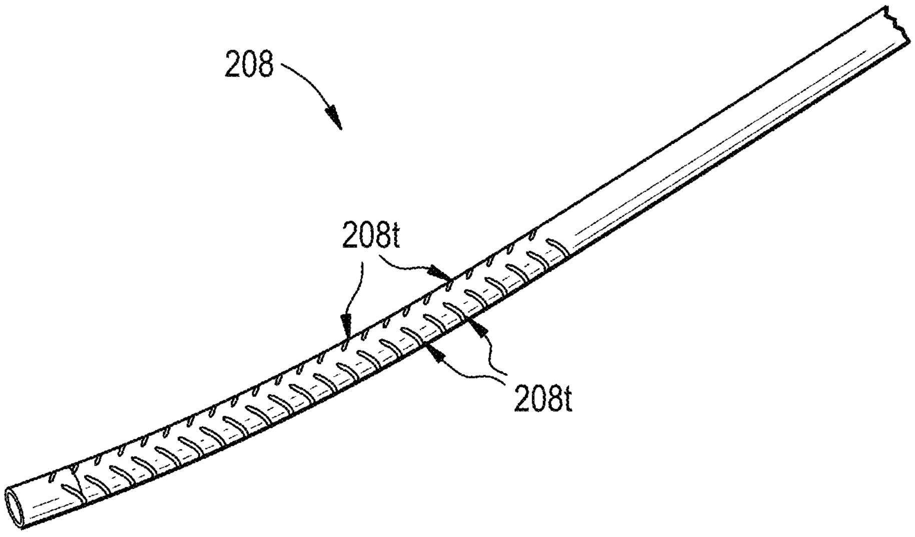
FIG. 41 is a perspective view of an outer shaft of the inserter tool of FIG. 36.

FIGS. 36 and 37 show the inserter 200 releasably coupled to the loading aid 122 of FIGS. 3-5. However, similar to that discussed above regarding the inserter 100 and the loading aid 122 of FIGS. 3-5, the inserter 200 of FIGS. 40 and 41 can be used with another loading aid or not used with a loading aid at all.

The curved outer shaft 208 in this illustrated embodiment is flexible, unlike the linear outer shaft 108 of the inserter tool 100 of FIGS. 1-5. In other embodiments, the curvature of an inserter's outer and inner shafts can be fixed. The outer shaft 208 being flexible facilitates the outer shaft's translation along the curved inner shaft 210. As shown in FIGS. 36-41, a distal portion of the outer shaft 208 includes a plurality of slits **208*t* formed therein that are configured to facilitate flexing of the outer shaft 208. The plurality of slits 208*t* in this illustrated embodiments includes two rows of crescent-shaped slits 208*t*, but another number of rows can be provided and/or the slits 208*t* can have another shape. Flexibility of the curved outer shaft 208 can be provided in another way. For example, the curved outer shaft 208 can include a plurality of score marks formed in the outer shaft 208 instead of including a plurality of slits. For another example, the curved outer shaft 208** can include a thinned portion of material in a distal portion thereof such that the outer shaft's sidewall is thinner than along a remainder for the outer shaft.

The retraction mechanisms 136, 236 of the inserter tools 100, 200 of FIGS. 1-5 (inserter 100) and FIGS. 36-39 (inserter 200) are each configured as a lever. However, as mentioned above, the retraction mechanism of an inserter tool can have another configuration. For example, the retraction mechanism can be configured as a rack and pinion mechanism. For another example, the retraction mechanism can be configured as a lead screw mechanism.

Figure 42:
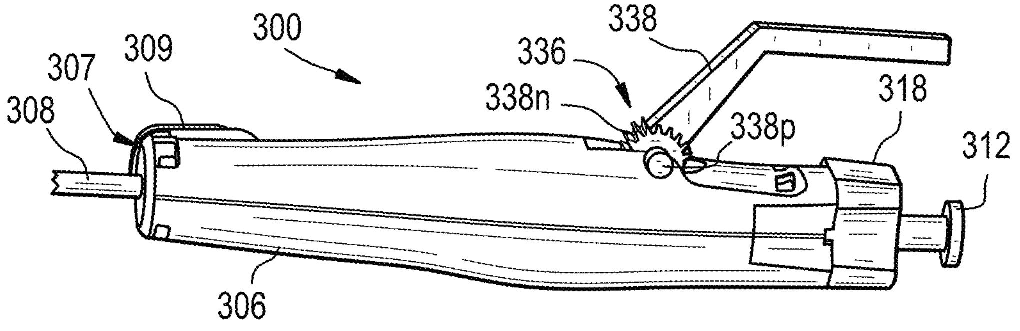
FIG. 42 is a perspective view of a proximal portion of another embodiment of an inserter tool.
Figure 43:
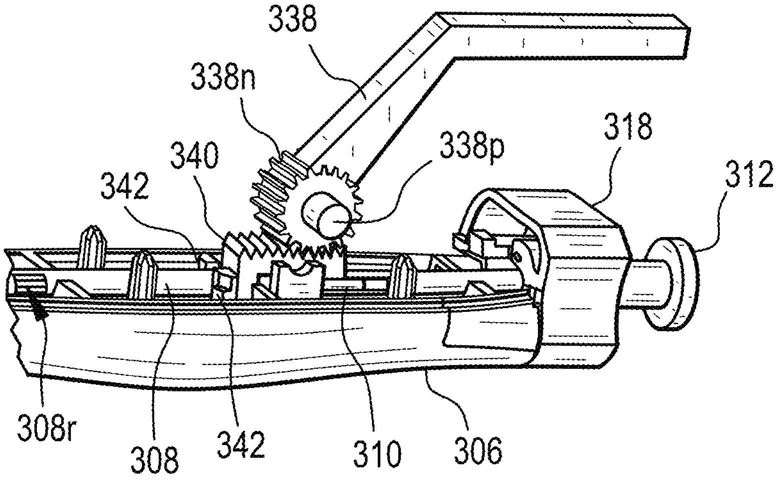
FIG. 43 is a perspective view of a proximal portion of the inserter tool of FIG. 42 with a handle of the inserter tool partially omitted.

FIGS. 42 and 43 illustrate one embodiment of an inserter tool 300 including a retraction mechanism 336 configured as a rack and pinion mechanism. The inserter tool 300 is for knotless anchor insertion in a soft tissue repair surgical procedure and is the same as the inserter tool 100 of FIGS. 1-5 except for the configuration of the retraction mechanism 336, e.g., is configured to insert an anchor into a bone of a patient to secure a soft tissue relative to the bone and includes a handle 306, an outer shaft 308 that extends distally from the handle 306 and includes a bushing (not shown in FIGS. 42 and 43), an inner shaft 310 that extends distally from the handle 306 and includes a notch formed therein that defines a suture retention channel (not shown in FIGS. 42 and 43), a suture retainer including a pliable member (not shown in FIGS. 42 and 43) that cooperates with the inner shaft 310 to define an enclosed passage (not shown in FIGS. 42 and 43), a suture retention member in the form of a groove 307 defined by the handle 306 and an elastomeric cleat 309 fixedly attached to the handle 306, a strike cap 312 that extends proximally from the handle 306, a locking mechanism 318 configured to lock the outer shaft 308 in position relative to the inner shaft 310 when the locking mechanism 318 is in a locked position, and a retraction mechanism 336 configured to cause the inserter tool 300 to be removed from within an anchor (not shown in FIGS. 42 and 43). The anchor can be the anchor 102 of FIG. 7 or can be another anchor, as discussed herein.

The retraction mechanism 336 includes a handle 338, a rack 340, and a base 342. The retraction mechanism handle 338 is configured to be moved by a user to actuate the retraction mechanism 336. Similar to the lever handle 136, the retraction mechanism handle 338 is disposed partially outside of the inserter handle 306 and partially inside the inserter handle 306. The rack 340 and the base 342 are disposed inside the inserter handle 306.

The retraction mechanism handle 338 includes a pair of opposed pins 338*p* configured to be seated in opposed holes defined by the inserter handle 306 and to rotate therein similar to the pins 138*p* of the lever handle 138. The retraction mechanism handle 338 also includes a pinion 338*n* in the form of a spur gear operably coupled to the rack 340 with teeth of the pinion 338*n* engaged with teeth of the rack 340. Movement of the retraction mechanism handle 338 causes the pinion 338*n* to rotate relative to the inserter handle 306, which causes the rack 340 to move due to the engagement of the teeth.

The rack 340 includes a pair of opposed rails (obscured in FIGS. 42 and 43) configured to be seated in opposed longitudinal channels formed in the outer shaft 308, similar to the rails 140*r* of the yoke 140 configured to be seated in the opposed longitudinal channels 108*c* formed in the outer shaft 108 discussed above. The rack's rails are each configured to be seated in one of a pair of opposed grooves of the inner shaft 310, similar to the yoke's rails 140*r* seated in the inner shaft's grooves 110*g* discussed above. The inner shaft 310 is disposed within the outer shaft's inner lumen, but the rails of the rack 340 are configured to extend through the outer shaft's longitudinal channels to be seated in the inner shaft's grooves. The rails of the rack 340 are configured to slide proximally within their respective longitudinal channels of the outer shaft 308 in response to actuation of the retraction mechanism 336. Because the rails of the rack 340 are seated in the grooves of the inner shaft 310, the proximal movement of the rack 340 is configured to cause corresponding longitudinal movement of the inner shaft 310 (and the suture retainer fixedly attached thereto) in the proximal direction relative to the outer shaft 308, the inserter handle 306, and the anchor releasably coupled to the inserter 300. The inner shaft 310 (and the suture retainer fixedly attached thereto) can thus be removed from within the anchor by moving proximally out of the anchor in response to actuation of the retraction mechanism 336. The outer shaft 308 is configured as a stop that stops proximal movement of the rack 340 when the rack 340, e.g., the rails thereof, abuts a proximal end of the outer shaft's longitudinal channels.

The retraction mechanism 336 is configured to move between an initial, unactuated positon and an actuated position, similar to the retraction mechanism 136 discussed above.

The lock base is fixedly attached to the push tube 308 by being seated in a pair of opposed grooves of the outer shaft 308, similar to the lever lock 142 seating in a pair of opposed grooves 108*g* of the outer shaft 108 discussed above. Thus, the distal movement of the push tube 308 is configured to cause corresponding longitudinal movement of the base 342 in the distal direction to move the base 342 distally. The locking mechanism 318, which is configured to lock the push tube 308 as discussed herein, is thus also configured to lock the base 342.

The outer shaft 308 in this illustrated embodiment includes a pair of opposed locking slots formed therein and a pair of opposed locking grooves 308*r* formed therein, similar to the pair of opposed slots 108*s* and the pair of opposed grooves 108*g* of the outer shaft 108 discussed above. The inserter handle 306 in this illustrated embodiment includes a pair of opposed fingers internal to the inserter handle 306 similar to the inserter handle 106 discussed above. Similar to that discussed above, the fingers seated in the locking slots are configured to help hold the outer shaft 308 in its proximal position prior to the strike cap 312 being struck to distally advance the outer shaft 308, and the fingers are each configured to releasably seat in the one of the outer shaft's locking grooves 308*r* after the outer shaft 308 has been distally advanced to distally advance the anchor, e.g., in response to striking of the strike cap 312.

In this illustrated embodiment the retraction mechanism handle 338 is configured to pivot about 90° from the unactuated position to the actuated position. Changing a pitch diameter of the spur gear 338*n* would change the pivot angle of the retraction mechanism handle 338 if another pivot angle was desired. For example, the pitch diameter of the spur gear 338*n* could be changed such that the retraction mechanism handle 338 is configured to pivot about 180° from the unactuated position to the actuated position. The retraction mechanism handle 338 being configured to pivot about 180° may make it easier for a user to hold the handle 306 of the inserter tool 300 after actuation of the retraction mechanism since the retraction mechanism handle 338 would be configured to be at its lowest profile relative to the handle 306 in each of the retraction mechanism's actuated position and unactuated position.

The outer and inner shafts 308, 310 of the inserter tool 300 can be linear, similar to the outer and inner shafts 108, 110 of the inserter 100 of FIGS. 1-5, or can be curved, similar to the outer and inner shafts 208, 210 of the inserter 200 of FIGS. 36-39.

The inserter 300 of FIGS. 42 and 43 can be used with the loading aid 122, used with another loading aid, or not used with a loading aid at all.

Figure 44:
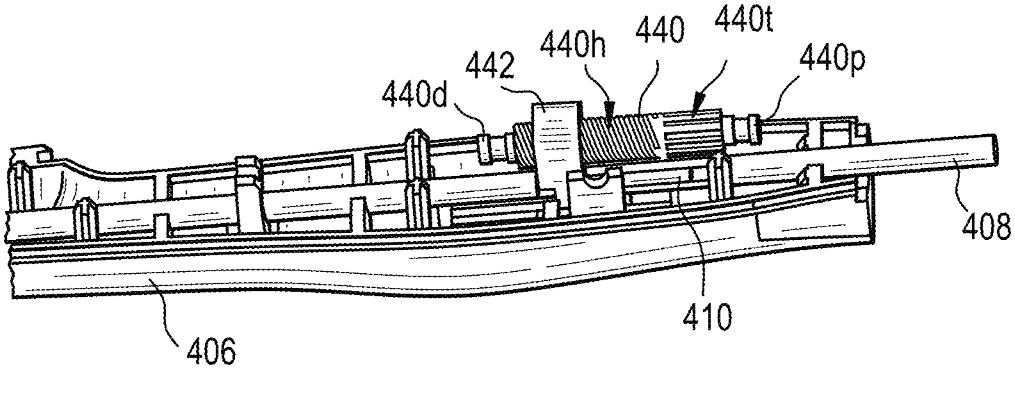
FIG. 44 is a perspective view of a portion of another embodiment of an inserter tool with a handle of the inserter tool partially omitted.
Figure 45:
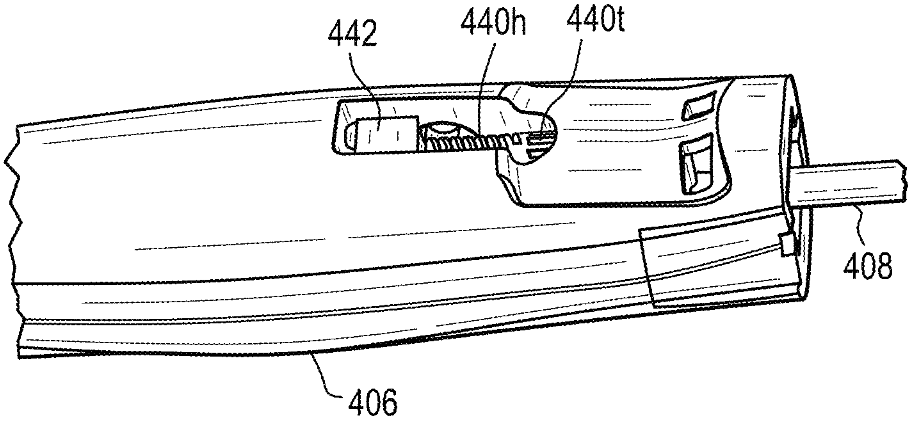
FIG. 45 is a perspective view of a portion of the inserter tool of FIG. 44 without the handle omitted.
Figure 46:
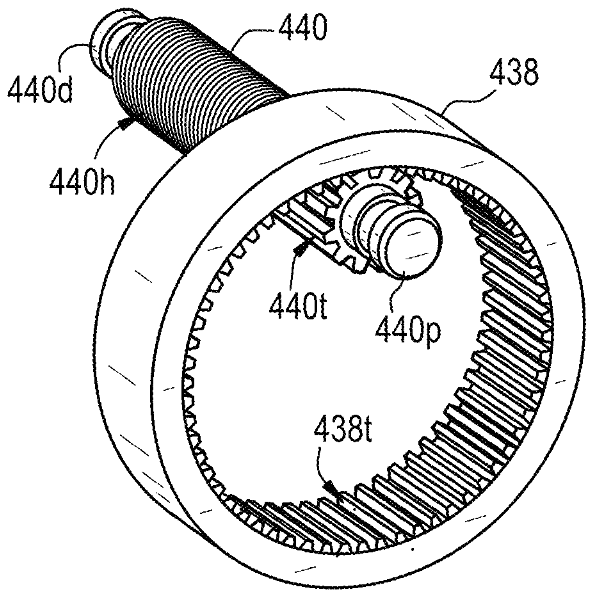
FIG. 46 is a perspective view of a ring actuator and a lead screw of the inserter tool of FIG. 44.
Figure 47:
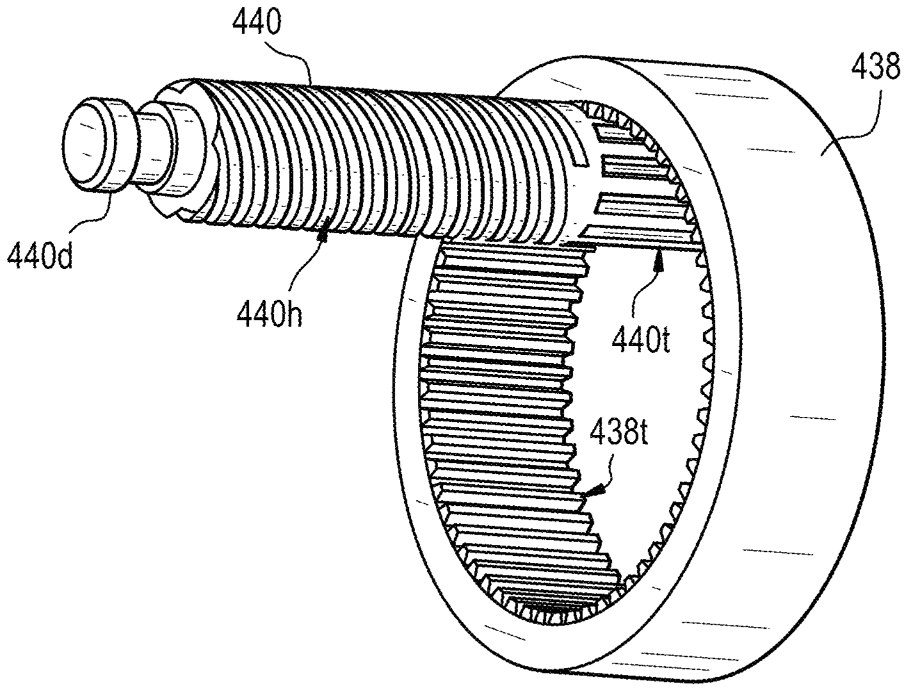
FIG. 47 is another perspective view of the ring actuator and the lead screw of FIG. 46.

FIGS. 44 and 45 illustrate one embodiment of an inserter tool 400 including a retraction mechanism configured as a lead screw mechanism. The inserter tool 400 is for knotless anchor insertion in a soft tissue repair surgical procedure and is the same as the inserter tool 100 of FIGS. 1-5 except for the configuration of the retraction mechanism 436, e.g., is configured to insert an anchor into a bone of a patient to secure a soft tissue relative to the bone and includes a handle 406, an outer shaft 408 that extends distally from the handle 406 and includes a bushing (not shown in FIGS. 44 and 45), an inner shaft 410 that extends distally from the handle 406 and includes a notch formed therein that defines a suture retention channel (not shown in FIGS. 44 and 45), a suture retainer including a pliable member (not shown in FIGS. 44 and 45) that cooperates with the inner shaft 410 to define an enclosed passage (not shown in FIGS. 44 and 45), a suture retention member (not shown in FIGS. 44 and 45), a strike cap (not shown in FIGS. 44 and 45) that extends proximally from the handle 406, a locking mechanism (not shown in FIGS. 44 and 45) configured to lock the outer shaft 408 in position relative to the inner shaft 410 when the locking mechanism 418 is in a locked position, and a retraction mechanism configured to cause the inserter tool 400 to be removed from within an anchor (not shown in FIGS. 44 and 45). The anchor can be the anchor 102 of FIG. 7 or can be another anchor, as discussed herein.

As shown in FIGS. 44-47, the retraction mechanism includes a ring actuator 438, a lead screw 440, and a guide 442. The ring actuator 438 is configured to be moved by a user to actuate the retraction mechanism, similar to the lever handles 138, 238 and the retraction mechanism handle 338 discussed above. The ring actuator 438 is disposed circumferentially around the handle 406 outside of the handle 406. The lead screw 440 and the guide 442 are disposed inside the handle 406.

The ring actuator 438 is operably coupled with the lead screw 440 with teeth 438*t* of the ring actuator 438 engaged with a teeth 440*t* of the lead screw 440. Movement of the ring actuator 438 causes the lead screw 440 to rotate relative to the handle 406, which causes the lead screw 440 to rotate due to the engagement of the teeth 438*t*, 440*t*.

Proximal and distal ends 440*p*, 440*d* of the lead screw 440 are rotatably attached to the handle 406. The lead screw 440 therefore cannot translate proximally or distally relative to the handle 406 but can rotate relative to the handle 406. A helical thread 440*h* of the lead screw 440 is threadably engaged with a thread (obscured in FIGS. 44 and 45) of the guide 442. The guide 442 is fixedly attached to the inner shaft 410, as discussed further below. The rotation of the lead screw 440 causes the guide 442 to move longitudinally in the proximal direction due to the engagement of the helical thread 440*h* of the lead screw 440 and the thread of the guide 442. The inner shaft 410 attached to the guide 442 thus also moves proximally.

The guide 442 includes a pair of opposed rails (obscured in FIGS. 44 and 45) configured to be seated in opposed longitudinal channels formed in the outer shaft 408, similar to the rails 140*r* of the yoke 140 configured to be seated in the opposed longitudinal channels 108*c* formed in the outer shaft 108 discussed above. The guide's rails are each configured to be seated in one of a pair of opposed grooves of the inner shaft 410, similar to the yoke's rails 140*r* seated in the inner shaft's grooves 110*g* discussed above. The inner shaft 410 is disposed within the outer shaft's inner lumen, but the rails of the guide 440 are configured to extend through the outer shaft's longitudinal channels to be seated in the inner shaft's grooves. The rails of the guide 440 are configured to slide proximally within their respective longitudinal channels of the outer shaft 408 in response to actuation of the retraction mechanism. Because the rails of the guide 440 are seated in the grooves of the inner shaft 410, the proximal movement of the guide 440 is configured to cause corresponding longitudinal movement of the inner shaft 410 (and the suture retainer fixedly attached thereto) in the proximal direction relative to the outer shaft 408, the handle 406, and the anchor releasably coupled to the inserter 400. The inner shaft 410 (and the suture retainer fixedly attached thereto) can thus be removed from within the anchor by moving proximally out of the anchor in response to actuation of the retraction mechanism. The outer shaft 408 is configured as a stop that stops proximal movement of the guide 440 when the guide 440, e.g., the rails thereof, abuts a proximal end of the outer shaft's longitudinal channels.

The guide 442 is configured as a lock configured to prevent the ring actuator 438 from being moved relative to the handle 406 and thus to prevent the guide 440 and the inner shaft 410 (and the suture retainer fixedly attached thereto) from moving relative to the handle 406. The engagement of the helical thread 440*h* of the lead screw 440 and the thread of the guide 442 prevents longitudinal translation of the guide 442, and thus of the outer shaft 408 attached thereto, except in response to rotation of the ring actuator 438.

The handle 406 can include a pair of opposed fingers 406*n* similar to the fingers 106*n* of the handle 105 discussed above, and the outer shaft 408 can include a pair of opposed locking slots 408 formed therein and a pair of opposed locking grooves formed therein similar to the pair of opposed slots 108*s* and the pair of opposed grooves 108*g* of the outer shaft 108 discussed above.

The outer and inner shafts 408, 410 of the inserter tool 400 can be linear, similar to the outer and inner shafts 108, 110 of the inserter 100 of FIGS. 1-5, or can be curved, similar to the outer and inner shafts 208, 210 of the inserter 200 of FIGS. 36-39.

The inserter 400 of FIGS. 44 and 45 can be used with the loading aid 122, used with another loading aid, or not used with a loading aid at all.

One skilled in the art will appreciate further features and advantages of the devices, systems, and methods based on the above-described embodiments. Accordingly, this disclosure is not to be limited by what has been particularly shown and described, except as indicated by the appended claims. All publications and references cited herein are expressly incorporated herein by reference in their entirety for all purposes.

The present disclosure has been described above by way of example only within the context of the overall disclosure provided herein. It will be appreciated that modifications within the spirit and scope of the claims may be made without departing from the overall scope of the present disclosure.

What is claimed is:

1. A surgical method, comprising:

positioning a distal end of an inner shaft of an inserter tool in a bone hole, the distal end of the inner shaft being releasably coupled to a suture such that the suture is also positioned in the bone hole;

moving an outer shaft of the inserter tool axially and distally relative to the inner shaft, thereby causing an anchor to slide along the inner shaft and be positioned in the bone hole such that the anchor traps the suture between an exterior surface of the anchor and a wall of the bone hole; and after the movement of the outer shaft axially and distally, causing the inner shaft to move axially and proximally relative to the outer shaft and the anchor such that the inner shaft is removed from the bone hole and the anchor and the suture remain in the bone hole.

2. The method of claim 1, wherein actuation of a lever of the inserter tool causes the inner shaft to move axially and proximally relative to the outer shaft and the anchor.

3. The method of claim 1, wherein of a rack and pinion mechanism of the inserter tool causes the inner shaft to move axially and proximally relative to the outer shaft and the anchor.

4. The method of claim 1, wherein actuation of a lead screw mechanism of the inserter tool causes the inner shaft to move axially and proximally relative to the outer shaft and the anchor.

5. The method of claim 1, wherein, before the movement of the outer shaft axially and distally, the inserter tool has an enclosed passage in which the suture is seated;

actuation of a retraction mechanism of the inserter tool causes the inner shaft to move axially and proximally relative to the outer shaft the anchor; and the actuation of the retraction mechanism also causes a pliable member of the inserter tool to move relative to the outer shaft and the anchor and to bend such that the enclosed passage opens.

6. The method of claim 1, wherein striking a strike cap of the inserter tool causes the movement of the outer shaft axially and distally;

actuation of a retraction mechanism of the inserter tool causes the inner shaft to move axially and proximally relative to the outer shaft and the anchor; and the striking of the strike cap causes a lock of the retraction mechanism to move from a locked position, in which the lock prevents the retraction mechanism from being actuated, to an unlocked position, in which the lock allows the retraction mechanism to be actuated.

7. The method of claim 6, wherein a holding mechanism of a handle of the inserter tool holds the outer shaft in position relative to the handle during the actuation of the retraction mechanism.

8. The method of claim 1, wherein the inserter tool comprises a handle that is positioned outside of a body of a patient with the distal end of the inner shaft positioned in the bone hole;

the outer shaft extends distally from the handle;

the inner shaft extends distally from the handle;

actuation of a retraction mechanism of the inserter tool causes the inner shaft to move axially and proximally relative to the outer shaft and the anchor; and the retraction mechanism is positioned outside of the body of the patient with the distal end of the inner shaft positioned in the bone hole.

9. A surgical method, comprising:

positioning a distal end of an inner shaft of an inserter tool and positioning a pliable member of the inserter tool in a bone hole;

moving an outer shaft of the inserter tool axially and distally relative to the inner shaft, thereby causing an anchor to move axially and distally and thereby be positioned in the bone hole such that the anchor traps a suture between an exterior surface of the anchor and a wall of the bone hole; and after the movement of the outer shaft axially and distally, causing the inner shaft and the pliable member to move axially and proximally relative to the outer shaft and the anchor such that the inner shaft and the pliable member are removed from the bone hole and the anchor and the suture remain in the bone hole, the pliable member unfolding during the axial and proximal movement of the pliable member.

10. The method of claim 9, wherein actuation of a lever of the inserter tool, a rack and pinion mechanism of the inserter tool, or a lead screw mechanism of the inserter tool causes the inner shaft and the pliable member to move axially and proximally relative to the outer shaft and the anchor.

* * * * *